(12) United States Patent
Gelbard

(10) Patent No.: US 6,687,640 B1
(45) Date of Patent: Feb. 3, 2004

(54) AIRBORNE AGENT CONCENTRATION ANALYSIS

(75) Inventor: Fred Gelbard, Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 199 days.

(21) Appl. No.: 10/000,930

(22) Filed: Oct. 23, 2001

(51) Int. Cl.[7] ............................................. F24F 7/007
(52) U.S. Cl. ...................... 702/122; 702/22; 702/23; 702/30; 702/31; 702/32; 702/24; 702/25; 454/229; 454/239
(58) Field of Search .................. 702/22–25, 30–32, 702/122, FOR 115, FOR 118, FOR 119, FOR 124, FOR 127–128; 454/49, 229, 236, 238, 255, 340, 239, 254; 55/385.2

(56) References Cited

U.S. PATENT DOCUMENTS

| | | | | |
|---|---|---|---|---|
| 4,416,748 A | * | 11/1983 | Stevens | 204/157.3 |
| 5,290,200 A | * | 3/1994 | Kiser | 454/229 |
| 5,349,567 A | * | 9/1994 | Reed | 367/100 |
| 5,511,006 A | * | 4/1996 | Tachibana et al. | 702/130 |
| 5,586,932 A | * | 12/1996 | Kiser | 454/229 |
| 5,597,354 A | * | 1/1997 | Janu et al. | 454/229 |
| 5,643,077 A | * | 7/1997 | Ayer | 454/54 |
| 5,668,562 A | * | 9/1997 | Cutrer et al. | 343/703 |
| 5,772,501 A | * | 6/1998 | Merry et al. | 454/256 |
| 5,791,983 A | * | 8/1998 | Robertson | 454/229 |
| 5,808,905 A | * | 9/1998 | Normann et al. | 703/2 |
| 5,976,010 A | * | 11/1999 | Reese et al. | 454/229 |
| 5,985,474 A | * | 11/1999 | Chen et al. | 429/17 |
| 6,076,048 A | * | 6/2000 | Gunther et al. | 702/51 |
| 6,102,793 A | * | 8/2000 | Hansen | 454/342 |
| 6,314,949 B1 | * | 11/2001 | DeGrazia et al. | 123/542 |
| 6,349,883 B1 | * | 2/2002 | Simmons et al. | 236/46 R |
| 2002/0072322 A1 | * | 6/2002 | Sharp et al. | 454/229 |
| 2002/0084900 A1 | * | 7/2002 | Peterson et al. | 340/573.1 |
| 2002/0098109 A1 | * | 7/2002 | Nelson et al. | 422/5 |
| 2002/0108605 A1 | * | 8/2002 | DeGrazia et al. | 123/538 |

OTHER PUBLICATIONS

Press, W. H., et al, Numerical Recipes (Cambridge University Press, Cambridge, 1992).

Hanson, R. J., "Linear Least Squares with Bounds and Linear Constraints," Sandia National Laboratories, Albuquerque, NM, SAND82–1517(1982).

Hanson, R. J., "Linear Least Squares with Bounds and Linear Constraints," SIAM J. Sol. Stat. Comput. 7 (3) 826–834 (1986).

Birchall, A, et al, "A Microcomputer Algorithm for Solving First–Order Compartmental Models Involving Recycling," Health Physics vol. 56, No. 6 (Jun.), pp. 857–868, 1989, Printed in the USA.

* cited by examiner

*Primary Examiner*—Marc S. Hoff
*Assistant Examiner*—Carol S. W. Tsai
(74) *Attorney, Agent, or Firm*—Robert D. Watson

(57) ABSTRACT

A method and system for inferring airborne contaminant concentrations in rooms without contaminant sensors, based on data collected by contaminant sensors in other rooms of a building, using known airflow interconnectivity data. The method solves a least squares problem that minimizes the difference between measured and predicted contaminant sensor concentrations with respect to an unknown contaminant release time. Solutions are constrained to providing non-negative initial contaminant concentrations in all rooms. The method can be used to identify a near-optimal distribution of sensors within the building, when then number of available sensors is less than the total number of rooms. This is achieved by having a system-sensor matrix that is non-singular, and by selecting that distribution which yields the lowest condition number of all the distributions considered. The method can predict one or more contaminant initial release points from the collected data.

29 Claims, 30 Drawing Sheets

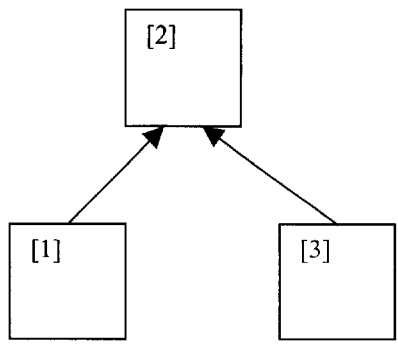

Figure 1

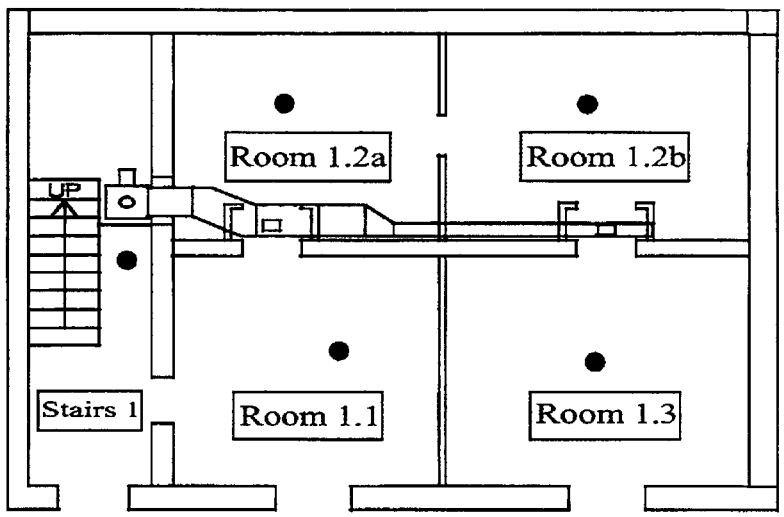

First floor of middle southern apartment in the German Village structure located at Dugway Proving Ground, shows duct work for HVAC system. Room labels corresponded to positions of propylene concentration point detectors (●) during propylene dispersion trials conducted as part of the 911-Bio ACTD Final Demonstration. Note the temporary wall constructed between rooms 1.2a and 1.2 b. The door in this wall was left open for all trials.

Figure 2

Second floor of middle southern apartment in the German Village structure located at Dugway Proving Ground, showing duct work for air handling system. Rooms were numbered to designate positions of propylene concentration point detectors (●) during propylene dispersion trials conducted as part of the 911-Bio ACTD Final demonstration.

AIRBORNE AGENT CONCENTRATION ANALYSIS

GOVERNMENT RIGHTS

The Government has rights to this invention pursuant to Contract No. DE-AC04-94AL85000 awarded by the U.S. Department of Energy.

BACKGROUND OF THE INVENTION

The present invention relates to a method and system for determining airborne contaminant concentrations in a building and for determining near-optimal placement of contaminant sensors within buildings.

Because of recent episodes of terrorist attacks, there is much interest in improving ability to sense and locate airborne toxic agents quickly and reliably. Therefore, improved sensing technology is being pursued. However, it is generally not cost effective or practical to have a chemical/biological sensor in every room of a building, as such sensors can be costly. Furthermore, given the significant probability that explosives may be involved that destroy some sensors, or that sensors may be intentionally sabotaged, it is important to have the automated ability to extract the most information from the remaining set of sensors. Accordingly, there is a great need for computer-based methods that can rapidly process whatever sensor data are being generated with the objective to rapidly determine agent concentrations throughout a building. This information can then be used to determine the source (or sources) of contamination, plan evacuations, plan mitigation and decontamination efforts, and provide initial conditions for detailed predictive modeling. Thus it is imperative that the calculations can be performed quickly with real-world data that are often incomplete and noisy.

Although smoke detectors are now so inexpensive that they are routinely mounted in many locations throughout commercial and government buildings, sensors for chemical and/or biological agents can be orders of magnitude more expensive, and therefore the cost of liberally distributing, maintaining, and monitoring many such sensors throughout a facility can be prohibitive. Thus there is a great incentive to optimally locate smaller numbers of sensors, while sacrificing as little accuracy as possible of the sensing capability of a liberally distributed system. Accordingly, an automated method for optimally locating a small number of expensive sensors is also needed.

The present invention provides both capabilities because it provides the ability to combine the airflow characteristics of a structure with limited sensor data into a form that can be solved using a least-squares algorithm.

SUMMARY OF THE INVENTION

The present invention relates to a method and system for inferring airborne contaminant concentrations in rooms without contaminant sensors, based on data collected by contaminant sensors in other rooms of a building, using known airflow interconnectivity data. The method solves a least squares problem that minimizes the difference between measured and predicted contaminant sensor concentrations with respect to an unknown contaminant release time. Solutions are constrained to providing non-negative initial contaminant concentrations in all rooms. The method can be used to identify a near-optimal distribution of sensors within the building, when the number of available sensors is less than the total number of rooms. This is achieved by having a system-sensor matrix that is non-singular, and by selecting that distribution which yields the lowest condition number of all the distributions considered. The method can predict one or more contaminant initial release points from the collected data.

The method can predict one or more contaminant initial release points from the received and the inferred concentration data. The received and the inferred concentration data can then be reported to a system for determining and communicating preferred escape routes for personnel in the building, and for determining the most efficient decontamination scheme.

The present invention is also of an apparatus for and method of placing a number of contaminant sensors that is less than the total number of rooms of a building, comprising: determining a distribution having a system-sensor matrix that is non-singular and having the lowest condition number of all distributions considered; and placing the available contaminant sensors in the determined distribution, wherein the contaminant sensor placement distribution is near-optimal with respect to inferring contaminant concentration data for rooms in the building not having a contaminant sensor from flow interconnectivity information for the building and contaminant concentration data from the contaminant sensors.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention.

FIG. 1 is a block diagram of an illustrative symmetric flow geometry.

FIG. 2 is a plan of the first floor geometry of the "German Village" structure (middle southern apartment) that is the subject of the examples; bullets indicate sensor locations.

FIG. 6 is a graph comparing predicted and measured concentrations in Room 1.2a.

FIG. 10 is a graph comparing predicted and measured concentrations in Room 2.2a.

FIG. 14 is a graph comparing predicted and measured concentrations in Stairs 2.

DETAILED DESCRIPTION OF THE INVENTION

Figure 3:
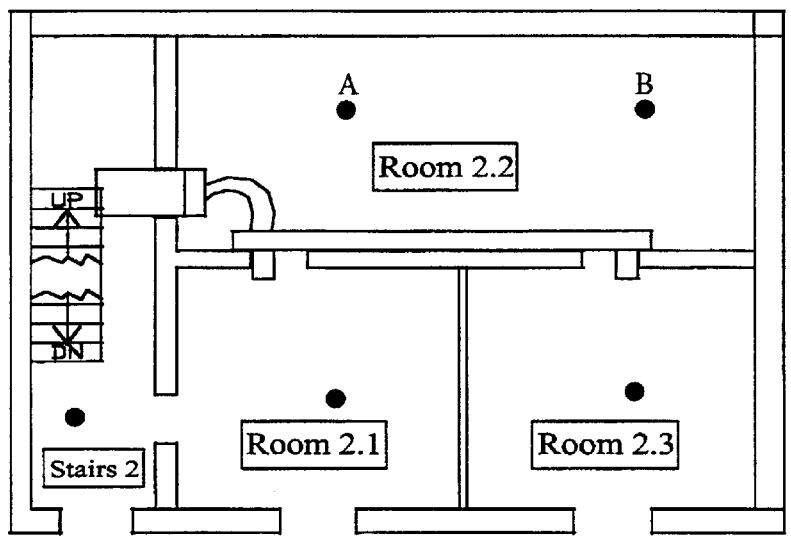
FIG. 3 is a plan of the second floor geometry of the "German Village" structure; bullets indicate sensor locations.

The present invention is a method and system and for determining contaminant concentrations in rooms without sensors in a building, using known airflow characteristics of the interconnected set of rooms, combined with time-dependent sensor measurements of airborne contaminants in rooms with sensors. The invention provides a fast and practical method for inferring contaminant concentrations in those rooms without sensors. The method can also be used to determine a near-optimal placement of a limited number of sensors in a building, where the number of sensors is less than the number of interconnected rooms.

The method of the present invention estimates agent (i.e. contaminant) concentrations in rooms without sensors, based on data from rooms with sensors. Examples of gaseous contaminants include chlorine gas, ammonia gas, nerve gas (VX, Sarin), and mustard gas. Examples of biological agents include anthrax spores, smallpox viruses, botulism toxins, molds, etc. The governing equations for agent concentrations in an interconnected, multi-room building are presented herein. The basic assumption is that each location is modeled as a well-mixed cell or volume with a time-dependent agent concentration. Typically, a room is represented with a single cell. A large room can be represented by several cells if greater spatial resolution is desired and the flows within the room are known. The airflow rates among cells are assumed to be known and constant. With these assumptions the governing equations can be solved analytically for the time-dependent cell concentrations in terms of the initial cell concentrations. Then a least-squares formulation is given for the unknown initial cell concentrations in terms of the measured cell concentrations. Next, the conditions needed to obtain a least-squares solution are presented. The invention also shows where to place sensors to avoid the singular cases in which sensor data will be inadequate to determine all initial cell concentrations.

The invention is also of a system and method for determining where best to place a limited number of (expensive) sensors in large, multi-room buildings to maximize the information gathering capability of the sensor array. By using this aspect of the invention, the limited data gathered by sensors will allow the determination of contaminant concentrations at locations without sensors, and provide more accurate predictions of contaminant transport.

The phrase "rooms of a building" is defined herein to broadly include at least two interconnected volumes in any generic structure. Hence, "rooms of a building" can include, for example, cavities or caverns inside a cave; mine shafts or corridors inside a mine; workspaces inside a space station, ship, submarine, or aircraft. The HVAC ducting of a building is also included in the definition of "rooms of a building."

The phrase "airflow" and "flow data" is defined herein to broadly include flow of any fluid from one interconnected volume to another within a structure. This includes the flow of gases other than air, and includes the flow of liquids (e.g., water), where the fluid flow rates are known from one volume to the next. Likewise, "airborne concentrations" also refers to the concentration of agents (contaminants) in a liquid or a gas other than air. The words "contaminants" and "agents" are used interchangeably.

The words "rooms" and "cells" and "locations" are used interchangeably herein. Unless otherwise stated, the phrase "rooms of a building" and "rooms" always refer to interconnected rooms that can exchange a fluid or gas (e.g., air) between rooms. The word "rooms", also includes junctions, intersections, or nodes of a HVAC ducting system. All of the rooms that are modeled need to be modeled as well-mixed volumes.

Each room may have one or more interconnections with other rooms in the building. The interconnections can be open or closed (e.g. a closed door or air vent).

The method of the present invention systematically searches through many possible sensor placement distributions to determine a near-optimal distribution. One can begin to appreciate the size of this task by enumerating the number of ways to distribute $N_s$ sensors in $N_c$ possible locations (i.e., cells or rooms). The number of such distributions is given by $$\binom{N_c}{N_s} = \frac{N_c!}{N_s!(N_c - N_s)!}. \tag{1}$$

Even for the simple problem of placing only 5 sensors in a building with 150 rooms, from Eq. (1) the possible number of sensor placement distributions is 591,600,030. If each configuration requires only 0.01 second of computer time to evaluate, this problem would require over 68 days of continuous computing to exhaustively explore all the possibilities and permutations. Clearly, it is generally not practical to test all possible sensor placement distributions for large multi-room buildings. Therefore, a more practical approach is not one that finds the absolute optimal distribution, but instead provides a near-optimal distribution that satisfies certain criteria.

Returning to the contaminant-determining aspect of the invention, for a flow network in which the agent (i.e., contaminant) is instantaneously uniformly mixed within a given cell, the concentration of agent in cell j, $C_j$, is governed by a mass balance on the agent's concentration:

$$\frac{dC_j}{dt} = A_{j,j}C_j + \sum_{\substack{k=1 \\ k \neq j}}^{N_c} A_{j,k}C_k \quad (j = 1, 2, \ldots, N_c) \tag{2}$$

where $N_c$ is the number of cells and t is the time from $t_0$. The initial time $t_0$ may be known, but for generality is considered to be an unknown in this work. The first term on the right represents the rate of agent leaving cell j, and thus $A_{j,j}$ is minus the volumetric flow rate out of cell j divided by the volume of cell j. The second term represents the rate at which agent enters cell j summed up from all of the other cells k (except for cell j), where k goes from 1 to $N_c$ (except for j). Thus the flow matrix element $A_{j,k}$ is the volumetric flow rate from cell k to cell j divided by the volume of cell j.

For example, let $V_j$ and $V_k$ be the volumes of cells j and k, respectively, and let $f_k$ be the volumetric flow rate from cell k to cell j. Then $dC_j/dt=f_kC_k/V_j$ and $dC_k/dt=-f_kC_k/V_k$. Therefore, $A_{j,k}=f_k/V_j$ and $A_{k,k}=-f_k/V_k$. It is assumed throughout this work that the flow matrix A is constant (or piecewise constant) and known.

For the initial condition $C_{k,0}=C_k(t=t_0)$, the solution to Eq. (2) provides $C_{j,i}$, the concentration in cell j at relative time $t_i-t_0$, which is $$C_{j,i} = \sum_{k=1}^{N_c} E_{j,k}(t_i)C_{k,0} \quad (j = 1, 2, \ldots, N_c). \tag{3}$$

The exponential matrix E, at relative time $t_i-t_0$ is given by $$E(t_i) = I + (t_i - t_0)A + \frac{((t_i - t_0)A)^2}{2!} + \frac{((t_i - t_0)A)^3}{3!} + \ldots \tag{4}$$

where I is the identity matrix, and A is the flow matrix defined in Eq. (2). An efficient method for calculating E that is used in this work has been given by Birchall, A., et al., "A Microcomputer Algorithm for Solving First-Order Compartmental Models Involving Recycling," *Health Physics*, 56 (6) 857–868 (1989). As shown below, for simple flow matrices E can be calculated analytically. Eq. (3) provides the concentrations in all cells given the cell concentrations at the initial time to (which is at a relative time of zero). Notice that Eq. (3) provides a linear relationship between the initial cell concentrations, and the cell concentrations at later times. Thus, under certain circumstances (to be explained below), this linear relationship can be inverted to determine the unknown initial concentrations in terms of measured concentrations.

In general, the objective is to determine $C_{k,0}$ (k=1, 2, . . . , $N_c$) and $t_0$ given sensor measurements $\tilde{C}_{j,i}$ in cells j=1, 2, . . . , $N_s$ at relative times $t_i-t_0$, where i=1, 2, . . . , $N_t$. (Multiple sensors in a cell are averaged, and thus $N_s \leq N_c$. For clarity, $N_s$ will be written as a constant, but in this work the number of operational sensors can also vary with time, for example, as sensors become inactivated, sabatoged, or damaged during the event.) Once $C_{k,0}$ and $t_0$ are determined, then all cell concentrations can be determined at any future time of interest by substituting the initial concentrations into Eq. (3). Thus, the determination of all the initial concentrations permits the determination of all future cell concentrations during the time that the flow rates are constant. (The method may be extended to include piecewise-constant flow rates, such as might be encountered when the HVAC airflow is turned off during the nighttime, or when the airflow is increased when the air conditioning system turns on.)

Because the concentrations in all rooms are not measured, Eq. (3) cannot be used directly to determine the initial concentrations. Instead, to construct the linear relationship between the measured concentrations and the unknown initial concentrations, extract $N_s$ rows from the exponential matrix for each relative time $t_i-t_0$, with the row numbers corresponding to the cells with operational sensors. Then these $N_t$ sets of $N_s$ rows can be stacked to form the matrix B with $N_s \times N_t$ rows and $N_c$ columns. The predicted concentrations in cells with sensors are therefore given by $BC_0$, where $C_0$ is the unknown vector of initial concentrations in all cells and is of length $N_c$. To determine $C_0$, equate the predicted concentrations to the measured concentrations to get the following system of linear algebraic equations $$BC_0 = \sum_{i=1}^{N_t} S_i. \tag{5}$$

$S_i$ is a vector of measured concentrations $\tilde{C}_{j,i}$ j=1, . . . , $N_s$ at relative time $t_i-t_0$, and is of length $N_s$. For a unique solution to Eq. (5), $N_s \times N_t = N_c$ and the determinant of B is nonzero. (if $N_s \times N_t < N_c$ there is no unique solution.) As measurements are made, $N_s \times N_t$ will become greater than $N_c$. When the rank of $B > N_c$, Eq. (5) can be solved for $C_0$ using a Least Squares algorithm.

A variety of numerical methods can be used to solve Least Squares problems. As illustrative, consider the solution in terms of the Normal Equations. These equations are obtained by multiplying on the left both sides of Eq. (5) by the transpose of B, $B^T$, to give $$B^T B C_0 B^T \sum_{i=1}^{N_t} S_i. \tag{6}$$

The system-sensor matrix is defined as $M=B^T B$. As will be shown, the system-sensor matrix is critical for determining if a sensor array is invertible. If the array is invertible, the system-sensor matrix may then also be used to optimally locate sensors. Fortunately, M can be determined without any concentration measurements. Only the airflow rates between interconnected cells, sampling locations, sampling times and cell volumes, are needed to determine the utility of a particular sensor array distribution. By evaluating the sensitivity of the condition number of M, one can determine the effectiveness of changing sampling locations and sampling times for determining the accuracy of inverted sensor array data.

Eq. (6) provides the needed linear relationship between the measured concentrations and the unknown initial concentrations. In component form, Eq. (6) is given by $$\sum_{k=1}^{N_c} C_{k,0} \sum_{i=1}^{N_t} \sum_{j=1}^{N_s} E_{j,m}(t_i) E_{j,k}(t_i) = \sum_{i=1}^{N_t} \sum_{j=1}^{N_s} \tilde{C}_{j,i} E_{j,m}(t_i) \quad (m = 1, 2, \ldots, N_c). \tag{7}$$

The solution to Eq. (6) provides the vector $C_0$ that minimizes F, where F is given by:

$$F = \sum_{j=1}^{N_s} \sum_{i=1}^{N_t} (\tilde{C}_{j,i} - C_{j,i})^2. \qquad (8)$$

The solution to Eq. (6) is equivalent to solving Eq. (5) in the least squares sense using algorithms discussed by Lawson, C. L., et al., *Solving Least Squares Problems* (SIAM, Philadelphia, 1995). To complete the minimization process of F, if $t_0$ is also unknown, it can be determined using a Golden Section algorithm (Press, W. H., et al., *Numerical Recipes* (Cambridge University Press, Cambridge, 1992)), coupled to a quadratic fitting scheme.

In summary, the invention minimizes the difference between the measured and predicted sensor concentrations with respect to $t_0$ and in the least squares sense. Using this minimization approach one can obtain an optimal solution by iterating on only one variable ($t_0$), coupled to a linear system of algebraic equations. This is a robust and computationally efficient method of solving the nonlinear-coupled system for $t_0$ and $C_0$.

There are two possible problems with the approach given above. First, there is no guarantee that the optimal solution will always provide nonnegative initial concentrations in all cells. This problem can result from noisy data or inaccuracies in modeling. A simple remedy is to constrain the solution to only nonnegative solutions (Hanson, R. J., "Linear Least Squares with Bounds and Linear Constraints," Sandia National Laboratories, Albuquerque, N.Mex., SAND82-1517 (1982); Hanson, R. J., "Linear Least Squares with Bounds and Linear Constraints," *SIAM J. Sci. Stat. Comput.* 7 (3) 826–834 (1986)). It is therefore preferred to use Hanson's NNLS (Nonnegative Least Squares) subroutine that guarantees nonnegative results. Hanson's NNLS subroutine is available from the SLATEC library (http://www.netlib.org/liblist.html).

The second potential problem is that the system-sensor matrix M can be singular. When this occurs, data from the sensor array produces a noninvertible matrix, M. There are two cases when M will be singular, and, hence, noninvertible. This discussion will now show with simple examples how these situations can occur, and more importantly, how to locate sensors to avoid these problems.

Consider a group of cells connected in a series, such that one cell vents into an adjoining cell, which vents into the next cell in the series. For this configuration, at least one sensor must be placed at the end of the series to ensure invertibility of M. To keep the algebra simple, one can demonstrate this concept with just two cells having the same volume and with "a" equal to the flow rate from cell [1] to cell [2] divided by the cell volume. The flow and exponential matrices for this simple case are given by $$A = \begin{bmatrix} -a & 0 \\ a & 0 \end{bmatrix} \text{ and} \qquad (9)$$

$$E(t_i) = \begin{bmatrix} \exp(-a(t_1 - t_0)) & 0 \\ 1 - \exp(-a(t_i - t_0)) & 1 \end{bmatrix}. \qquad (10)$$

For this simple case, the exponential matrix defined in Eq. (4) can be readily determined as given in Eq. (10). However, the exponential matrix is determined numerically for larger and more complicated flow matrices. If a sensor is placed in cell [1] but not cell [2], then the matrices B and $M \equiv B^T B$ are given by $$B = \begin{bmatrix} \exp(-a(t_1 - t_0)) & 0 \\ \exp(-a(t_2 - t_0)) & 0 \\ \exp(-a(t_3 - t_0)) & 0 \\ \vdots & \vdots \\ \exp(-a(t_{N_t} - t_0)) & 0 \end{bmatrix} \text{ and} \qquad (11)$$

$$M = \begin{bmatrix} \sum_{i=1}^{N_t} \exp(-2a(t_i - t_0)) & 0 \\ 0 & 0 \end{bmatrix}. \qquad (12)$$

From Eq. (12) one sees that no matter how many measurements are taken, the system-sensor matrix M will always be singular. This is thus a poorly designed sensor system and the initial concentrations cannot be uniquely determined.

Alternatively, had the sensor been placed at the end of the series, in this case in cell [2], the A and E matrices would be the same as given in Eqs. (9) and (10), but the matrices B and M would be $$B = \begin{bmatrix} 1 - \exp(-a(t_1 - t_0)) & 1 \\ 1 - \exp(-a(t_2 - t_0)) & 1 \\ 1 - \exp(-a(t_3 - t_0)) & 1 \\ \vdots & \vdots \\ 1 - \exp(-a(t_{N_t} - t_0)) & 1 \end{bmatrix} \text{ and} \qquad (13)$$

$$M = \begin{bmatrix} \sum_{i=1}^{N_t} [1 - \exp(-a(t_i - t_0))]^2 & \sum_{i=1}^{N_t} [1 - \exp(-a(t_i - t_0))] \\ \sum_{i=1}^{N_t} [1 - \exp(-a(t_i - t_0))] & N_t \end{bmatrix}. \qquad (14)$$

In general for $N_t > 1$, M in Eq. (14) will be nonsingular, and a unique solution can be obtained. Thus, one sees that even for the same flow geometry and number of sensors, sensor locations can dramatically affect the utility of the data.

To emphasize the importance of locating sensors at the end of a series, consider a series with many cells. Placing a sensor in all cells but the last cell would still provide a singular system-sensor matrix M. However, with just one sensor at the end of the series the system-sensor matrix would not be singular. Although M would not be singular, one still should avoid ill-conditioned matrices so that the estimated initial concentrations are not very sensitive to noise in the data.

A second configuration to avoid is locating sensors only in symmetry cells. Consider the three-cell configuration shown in FIG. 1 in which cells [1] and [3] vent into cell [2]. Intuitively, cell [2] would appear to be the appropriate cell for a sensor. Cell [2] is at the end of two series, one series consisting of cells [1] and [2], and the second series consisting of cells [3] and [2]. Therefore, based on the conclusions given on serially connected cells, the appropriate location for a sensor would seem to be at the end of these series, which is cell [2].

If the flow rates divided by the cell volumes from cells [1] and [3] are equal, then cell [2] is a symmetry cell. Even though cell [2] is at the end of two serially connected cells, because it is a symmetry cell, locating a sensor only in cell [2] is actually a bad choice because sensor data from symmetry cells alone are not invertible. The symmetry can be broken if there are different cell flow rates divided by cell volumes for cells [1] and [3]. With no symmetry, placing a sensor in cell [2] would be adequate for inverting data from the sensor. With symmetry, at least two sensors are required, one in cell [2] and another sensor in either cells [1] or [3]. A poor choice for these two sensors would be to locate them in cells [1] and [3]. In this case there would not be a sensor at the end of a series, and therefore the system would also not be invertible. The least efficient use of sensors to solve symmetry problems would be to place a sensor in each cell, thus requiring three sensors.

To prove the symmetry problem mathematically, one can determine the flow matrix A for the configuration in FIG. 1 as $$A = \begin{bmatrix} -\alpha & 0 & 0 \\ \alpha & 0 & \alpha \\ 0 & 0 & -\alpha \end{bmatrix}. \quad (15)$$

where "a" is a constant. This flow matrix is simple enough such that the exponential matrix defined in Eq. (4) can be readily determined as $$E(t_i) = \begin{bmatrix} \exp(-\alpha(t_i - t_0)) & 0 & 0 \\ 1 - \exp(-\alpha(t_i - t_0)) & 1 & 1 - \exp(-\alpha(t_i - t_0)) \\ 0 & 0 & \exp(-\alpha(t_i - t_0)) \end{bmatrix}. \quad (16)$$

For a sensor in cell [2], the B matrix is formed by stacking the second row from the exponential matrix for each time measurement. In this case one has $$B = \begin{bmatrix} 1 - \exp(-\alpha(t_i - t_0)) & 1 & 1 - \exp(-\alpha(t_i - t_0)) \\ \vdots & \vdots & \vdots \\ 1 - \exp(-\alpha(t_{N_t} - t_0)) & 1 & 1 - \exp(-\alpha(t_{N_t} - t_0)) \end{bmatrix} \quad (17)$$

Therefore, the system-sensor matrix $M = B^T B$, is given by $$M = \begin{bmatrix} \sum_{i=1}^{N_t}[1 - \exp(-\alpha(t_i - t_0))]^2 & \sum_{i=1}^{N_t}[1 - \exp(-\alpha(t_i - t_0))] & \sum_{i=1}^{N_t}[1 - \exp(-\alpha(t_i - t_0))]^2 \\ \sum_{i=1}^{N_t}[1 - \exp(-\alpha(t_i - t_0))] & 1 & \sum_{i=1}^{N_t}[1 - \exp(-\alpha(t_i - t_0))] \\ \sum_{i=1}^{N_t}[1 - \exp(-\alpha(t_i - t_0))]^2 & \sum_{i=1}^{N_t}[1 - \exp(-\alpha(t_i - t_0))] & \sum_{i=1}^{N_t}[1 - \exp(-\alpha(t_i - t_0))]^2 \end{bmatrix} \quad (18)$$

Notice that the first and third rows of the system-sensor matrix are identical regardless of the number of measurements $N_t$. Similarly, the first and third columns are identical. Thus M is singular and not invertible. The symmetry of M is due to the symmetry of the problem.

The criteria for selecting a near-optimal sensor placement distribution can be based on a combination of safety, security, and economic considerations. However, the criteria must be mathematically defined such that a search method has a basis for comparing different distributions. The present invention is further of a system and method for determining a near-optimal sensor placement distribution that can be used to provide accurate initial concentrations throughout a facility from a limited number of sensors, regardless of where a contaminant (or contaminants) is released in the facility.

To determine the initial concentrations the system-sensor matrix M must be nonsingular. The matrix M is computed from the flow rates between rooms, room volumes, sensor locations, and sensing times, which are all independent of the contaminant release time and location. If M is nonsingular, then theoretically M can be inverted to obtain a unique solution for the initial concentrations. For computational purposes it is preferred to require that M be well conditioned for a unique solution. The conditioning of M can be assessed by calculating the condition number, $C_n$, which is defined as $$C_n = \|M\| \|M^{-1}\| \quad (19)$$

where $\|M\|$ is the norm of M, and $\|M^{-1}\|$ is the norm of the inverse of M. (A typical norm is the maximum column sum of the absolute values of the elements of M.) The larger the condition number, the closer the matrix is to being singular, and hence the more difficult it will be to accurately determine the initial concentrations. Thus the criterion for absolute optimality is that M has the smallest condition number among all the possible distributions for a given number of sensors. However, an exhaustive search through all possible distributions may not be practical. Therefore, one may instead seek a near-optimal distribution in which $C_n$ is smallest among the distributions evaluated, and for the numerical technique used in this work to solve the least squares problem, this value of $C_n$ is not too much larger than the inverse of machine round-off error. The maximum acceptable value for $C_n$ will thus depend on both machine precision and the numerical method used to solve the least squares problem. For calculations used in an embodiment this invention with computations in double precision or greater, one can expect accurate results with $C_n$ up to on the order of $10^9$. In summary, the criteria for a near-optimal distribution can now be mathematically stated as requiring that (a) the system-sensor matrix has the lowest condition number of all the sensor placement distributions considered, and (b) that this lowest condition number be small enough such that machine round-off error is unimportant. If the sensor placement distribution satisfies these two criteria, the resulting sensor data can provide enough information to determine contaminant concentrations throughout a building. Hence a near-optimal sensor placement distribution is provided by the present invention.

The preferred search method to find a sensor distribution that satisfies these criteria is to start with the liberally distributed system of a sensor in every room. Thus, initially the number of sensors to test a distribution equals the number of rooms. Let $N_{test}$ be this number which starts with a value of $N_c$. This initial distribution must of course have a well-conditioned system sensor matrix, or there is no point in continuing the search. Next, for each sequence the following two steps are repeated $N_{test}$ times.

(1) Remove a sensor from a room (that has not previously had its sensor removed in this sequence), then evaluate and store the condition number for the system of $N_{test} - 1$ sensors; then (2) Replace the sensor in step (1).

After completing these two steps $N_{test}$ times, a sensor is permanently removed from the room for which the condition number increased the least when its sensor was removed. The next sequence is started by decrementing $N_{test}$ by 1, and steps (1) and (2) are repeated $N_{test}$ times again. The entire process is continued until either the second near-optimality criterion (criterion (b) described above) is violated, or $N_{test}$ is equal to the number of sensors that are available.

The number of distributions that are evaluated by the invention can be determined as follows. The number of distributions to evaluate in the first sequence is $N_c$. The second sequence will require evaluating $N_c-1$ distributions. In general, for the "i-th" sequence, $N_c-i+1$ distributions need to be evaluated. Thus, if $N_{out}$ sensors are removed, the total number of distributions evaluated by this algorithm is given by $$N_c + (N_c - 1) + (N_c - 2) + \cdots + (N_c - N_{out} + 1) = \quad (20)$$
$$N_c N_{out} + \frac{(N_{out} - 1)N_{out}}{2}.$$

For a building with 150 rooms and 5 sensors, $N_{out}=145$, and only 32,190 distributions need to be considered. This is a far more tractable problem than an exhaustive search, which would require the evaluation of 591,600,030 condition numbers. However, there is a risk in using this one-sensor-at-a-time search. It is possible that a distribution exists with a smaller condition number for the same number of sensors. Therefore, to generalize the method, instead of removing just one sensor, $N_r$ sensors may be considered for removal where $N_r$ is 1 or more. Then for each sequence, the condition number for removing all combinations of $N_r$ sensors can be evaluated. In the limit of $N_r=N_{out}$, the search algorithm reduces to an exhaustive search. For the test case presented below, it is believed that $N_r=1$ was adequate.

A genetic algorithm (Goldberg, D. E., *Genetic Algorithms in Search, Optimization, and Machine Learning* (Addison-Wesley Publishing Co., Inc., 1989); Davis, L., *Handbook of Genetic Algorithms* (Van Nostrand Reinhold, 1991)) can also be used for this purpose. Genetic algorithms (GA) are general-purpose stochastic optimization heuristics that search using a population of search points. These methods generate new trial points using (a) recombination operators that combine two (or more) points in the population, and (b) mutation operators that make a small change to a single point is It is preferred to employ a GA that searches through points representing subsets of sensors that were used to form the system-sensor matrix. However, a GA is believed not able to find better solutions than the preferred method of the invention, and in many cases will converge to the same solution as the one-sensor-at-a-time search method.

An alternative method is to start with only a few sensors that seem to be at critical locations and would avoid a singular matrix. Examples of critical locations include nodes or junctions in the HVAC ducting system. Then the search can test the addition of sensors one-at-a-time until the condition number is low enough to satisfy the near-optimality criteria. This complementary search approach has the potential problem that the initial system-sensor matrix may be singular or so ill-conditioned that there may not be any room at the start of the search for which adding a sensor has a discernable effect.

To summarize, the present invention provides a rapid and robust system and method for estimating contaminant concentrations in a building with interconnected rooms given time-dependent sensor measurements at other locations, and the flow characteristics of the building. The invention provides a least-squares estimate of all room concentrations that is guaranteed to be nonnegative. This information can then be used to plan evacuations and provide initial conditions for more detailed predictive modeling.

Furthermore, because chemical and biological sensors are expensive, optimally locating a few such sensors in a large multi-room building is of great importance. In general, sensor placement should be made to minimize loss-of-life in the event of a toxic agent release. However, this desirable objective can be highly case specific, and does not provide a clearly defined mathematical basis for comparing different sensor placement distributions.

If information gathering and predicting contaminant concentrations is the objective, then sensor placement distributions can be compared quantitatively. Unfortunately, the number of possible distributions to evaluate can be prohibitively large. Thus an exhaustive search for the absolute optimum may not be practical. Accordingly, the present invention provides a near-optimal search system and method. The invention preferably starts with a sensor in every possible location, and then sequentially removes the least important sensors. Sensor removal is continued until either the condition number of the system-sensor matrix is too large to accurately calculate the initial concentrations throughout a building, or the number of sensors desired is reached (e.g., as limited by cost considerations).

The present invention is useful in a wide variety of applications, including defense of persons and property against terrorist activity, industrial accidents, and natural disasters, and occupational safety and health forensics. The method of the invention are preferably implemented on personal computer platforms with appropriate connectivity to real-time sensor data, and so can be inexpensively implemented. As is readily understood by one of ordinary skill in the art, the method can be implemented in any of a number of computer languages (e.g., a version of FORTRAN), optionally in combination with available least squares computation packages.

Industrial Applicability

The invention is further illustrated by the following non-limiting examples.

EXAMPLE 1

Figure 4:
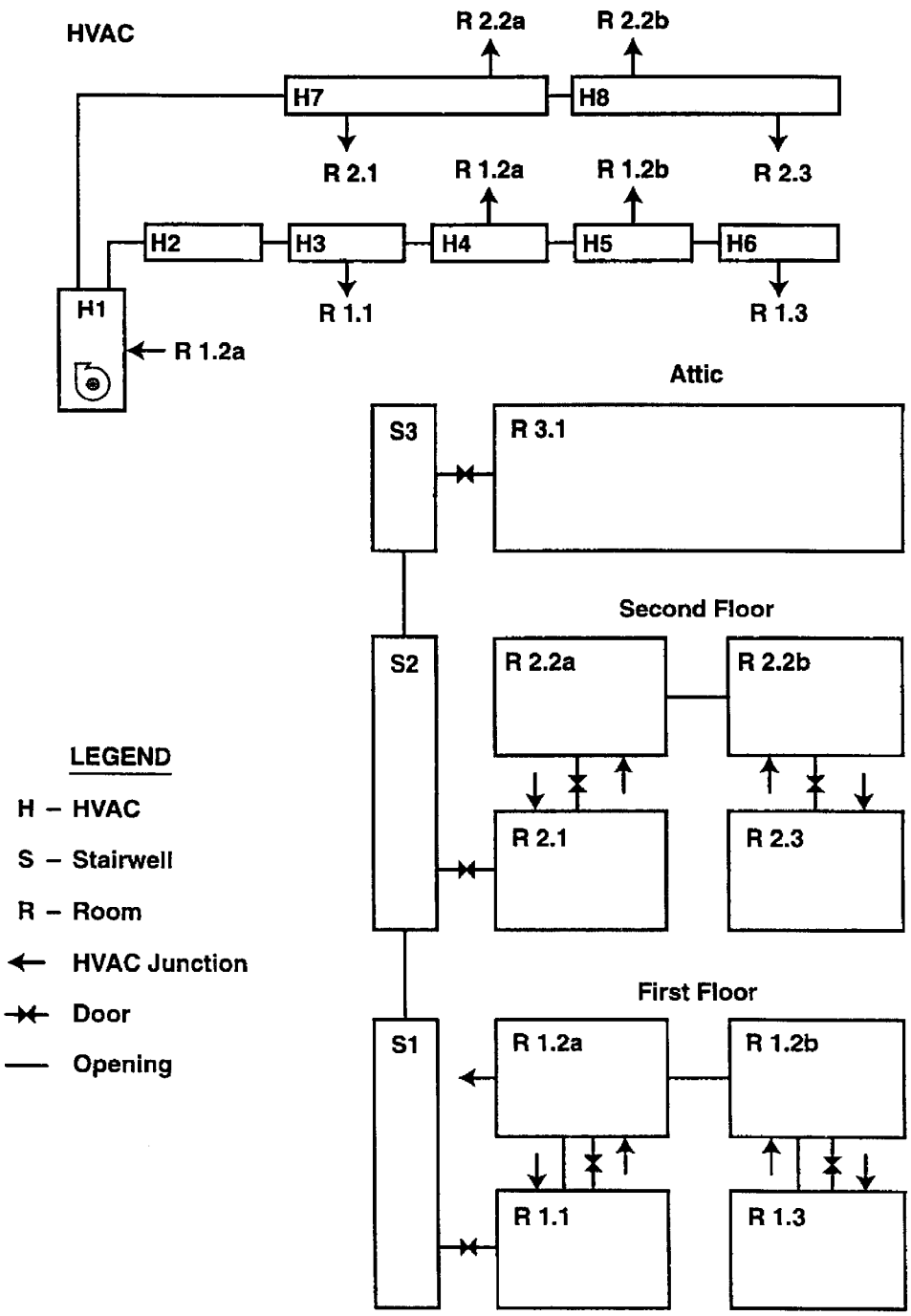
FIG. 4 is a flow interconnectivity diagram for the "German Village" structure.
Figure 5:
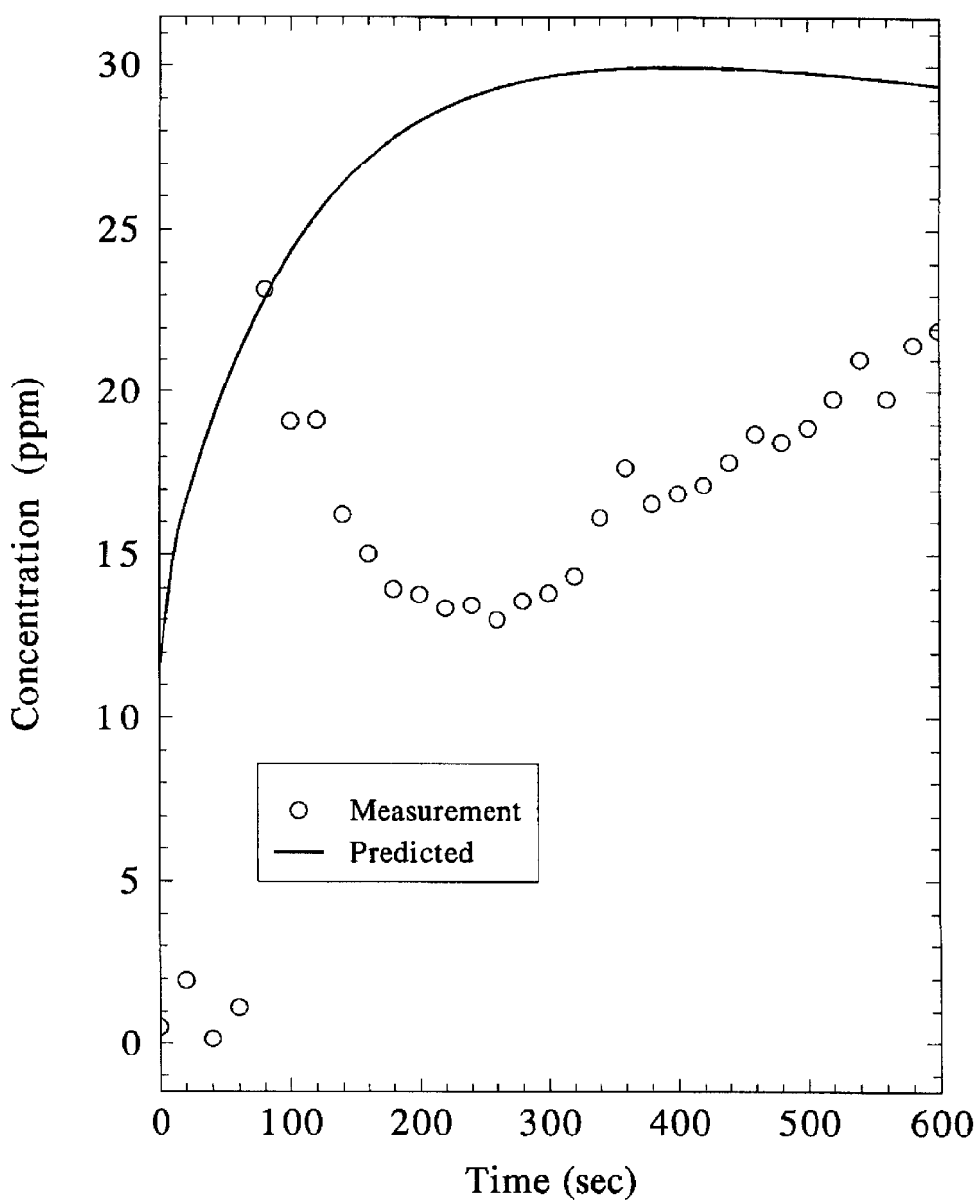
FIG. 5 is a graph in regard to Example 1 comparing predicted and measured concentrations in Room 1.1.
Figure 6:
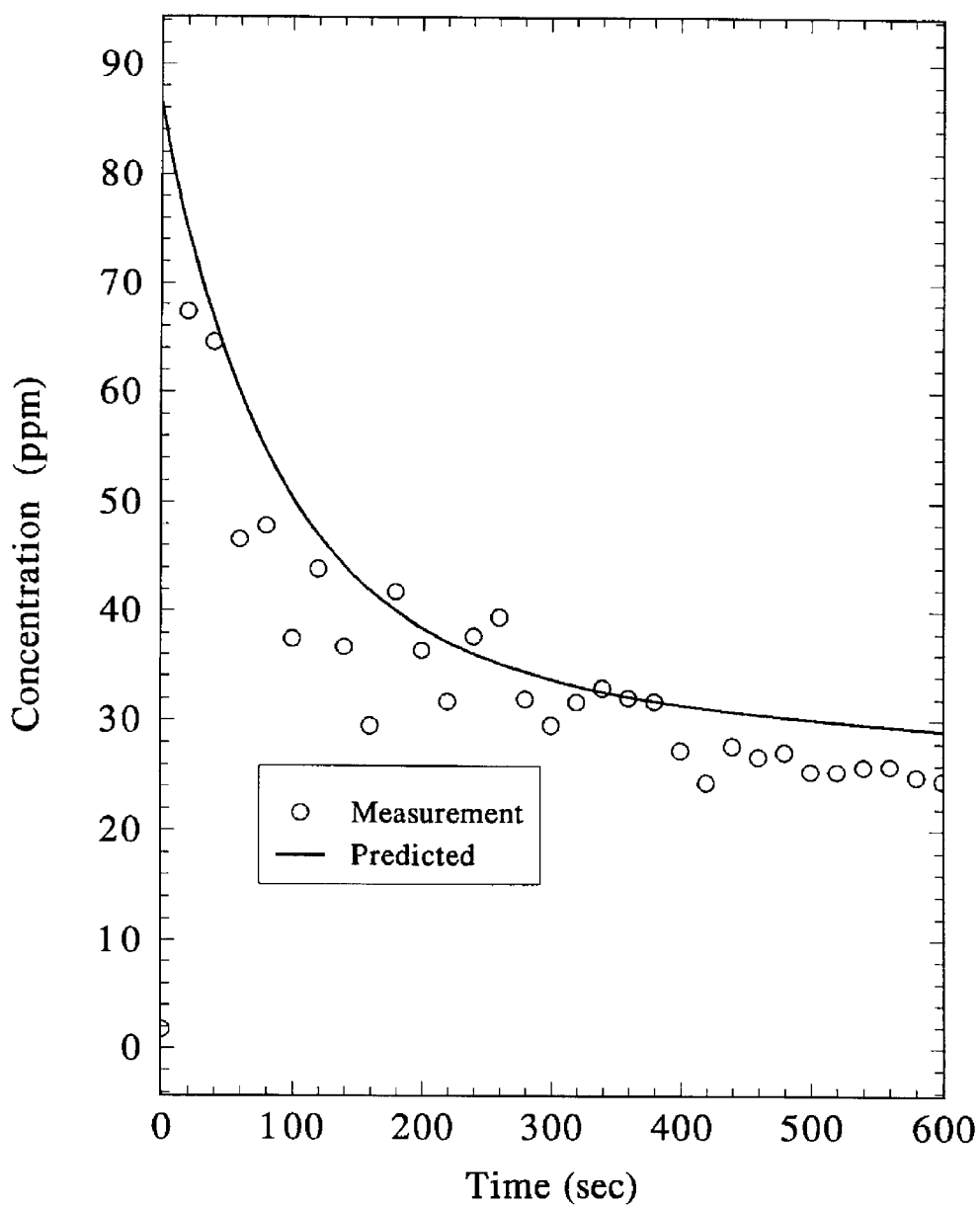
Figure 7:
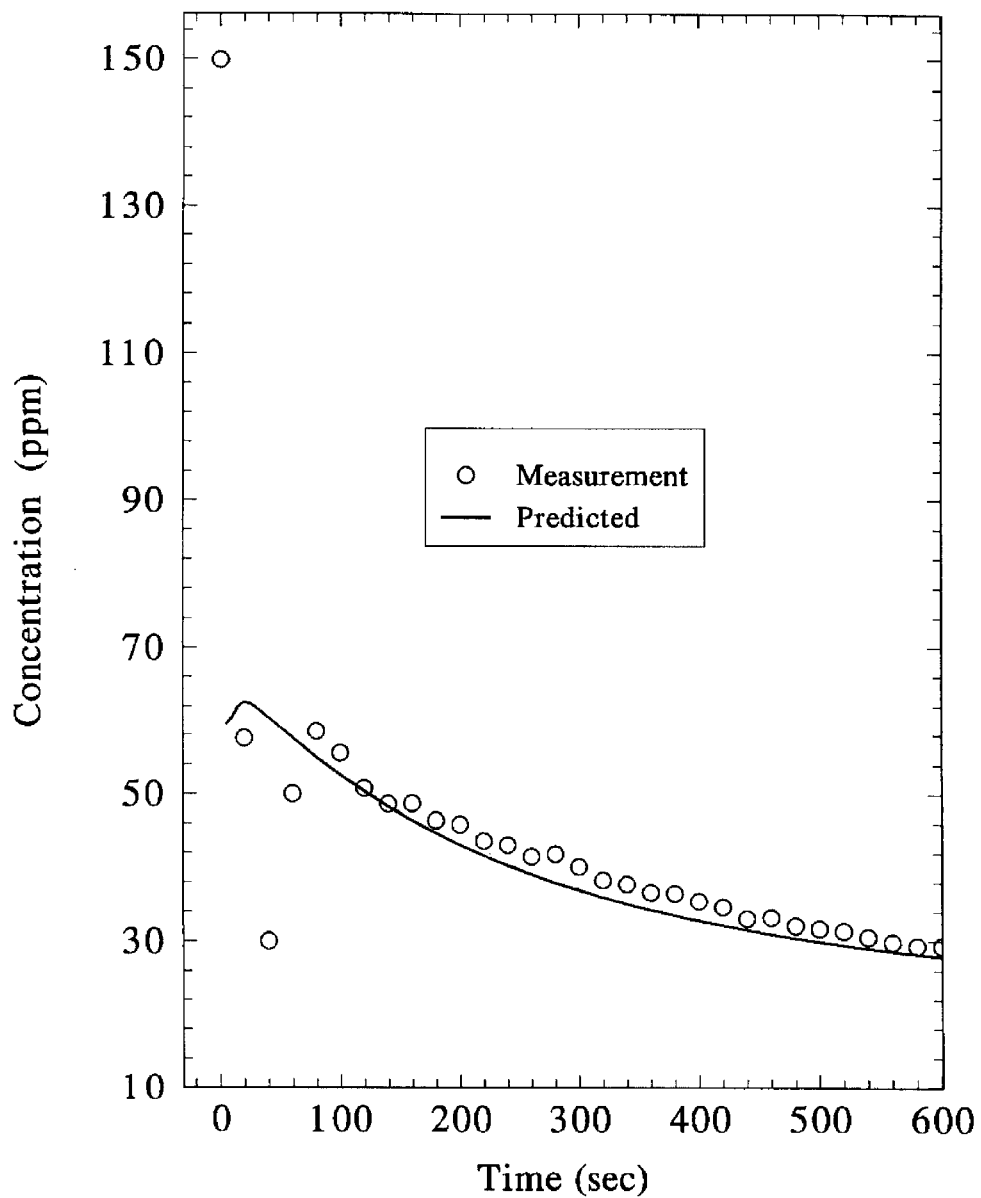
FIG. 7 is a graph comparing predicted and measured concentrations in Room 1.2b.
Figure 8:
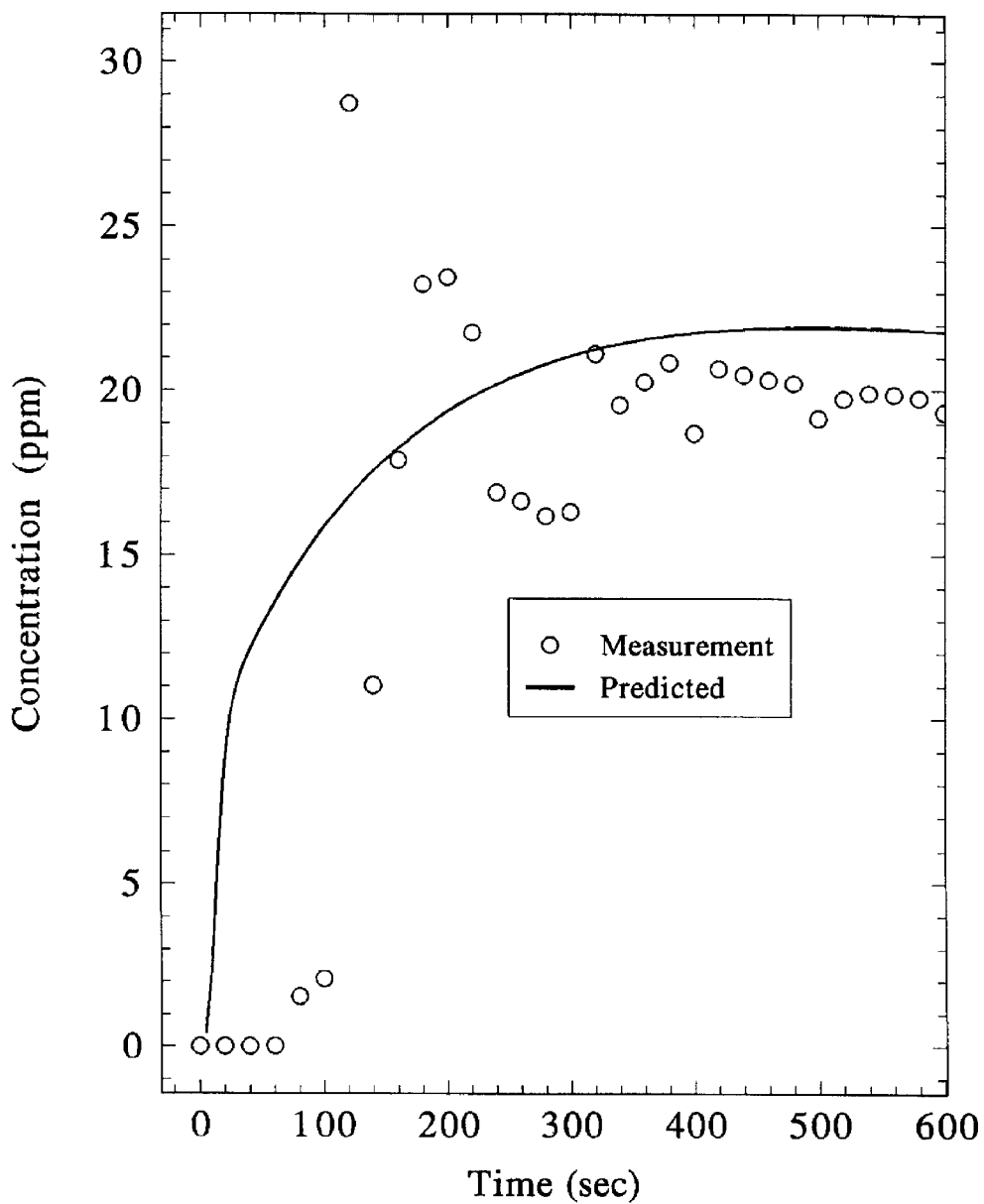
FIG. 8 is a graph comparing predicted and measured concentrations in Room 1.3.
Figure 9:
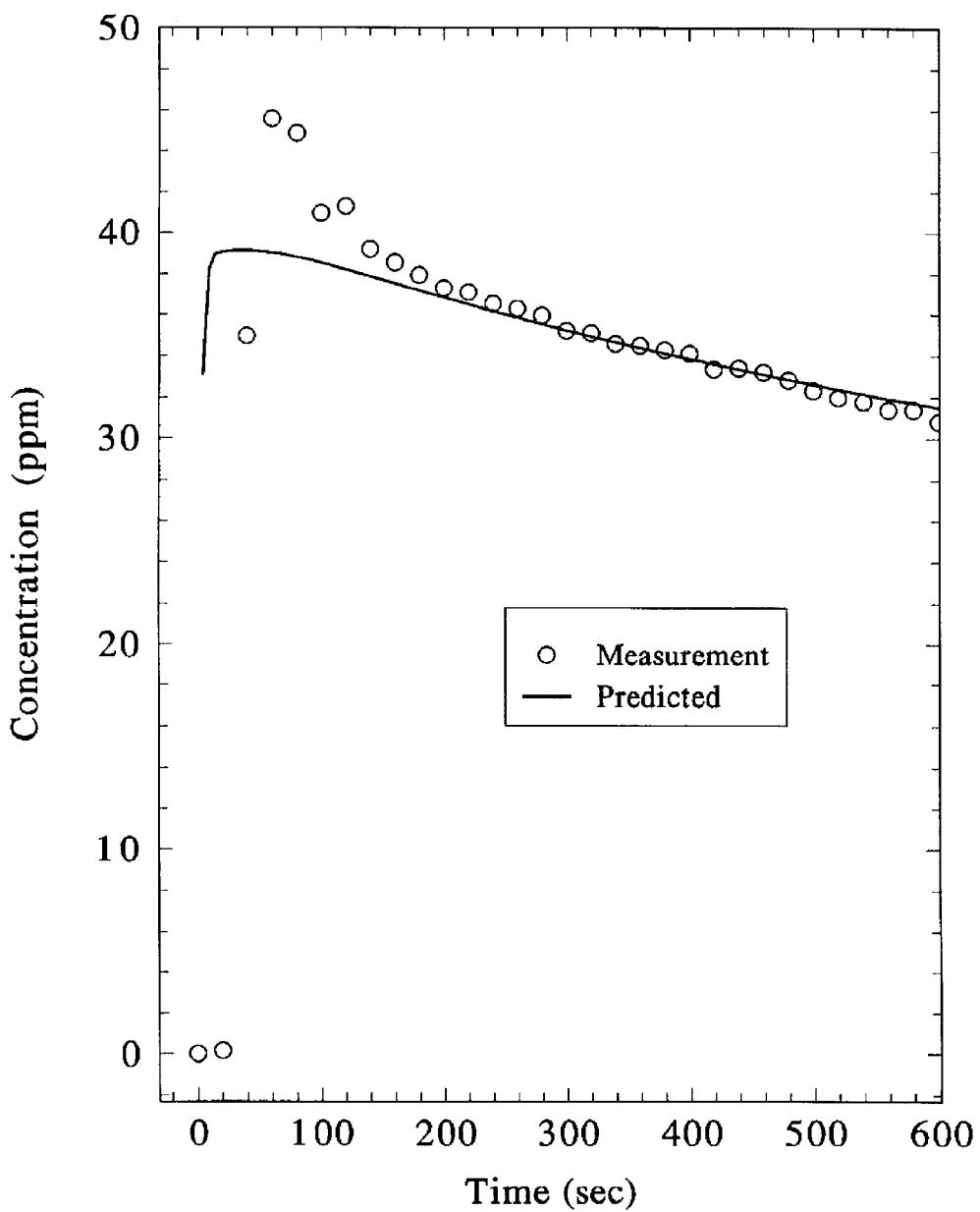
FIG. 9 is a graph comparing predicted and measured concentrations in Room 2.1.
Figure 10:
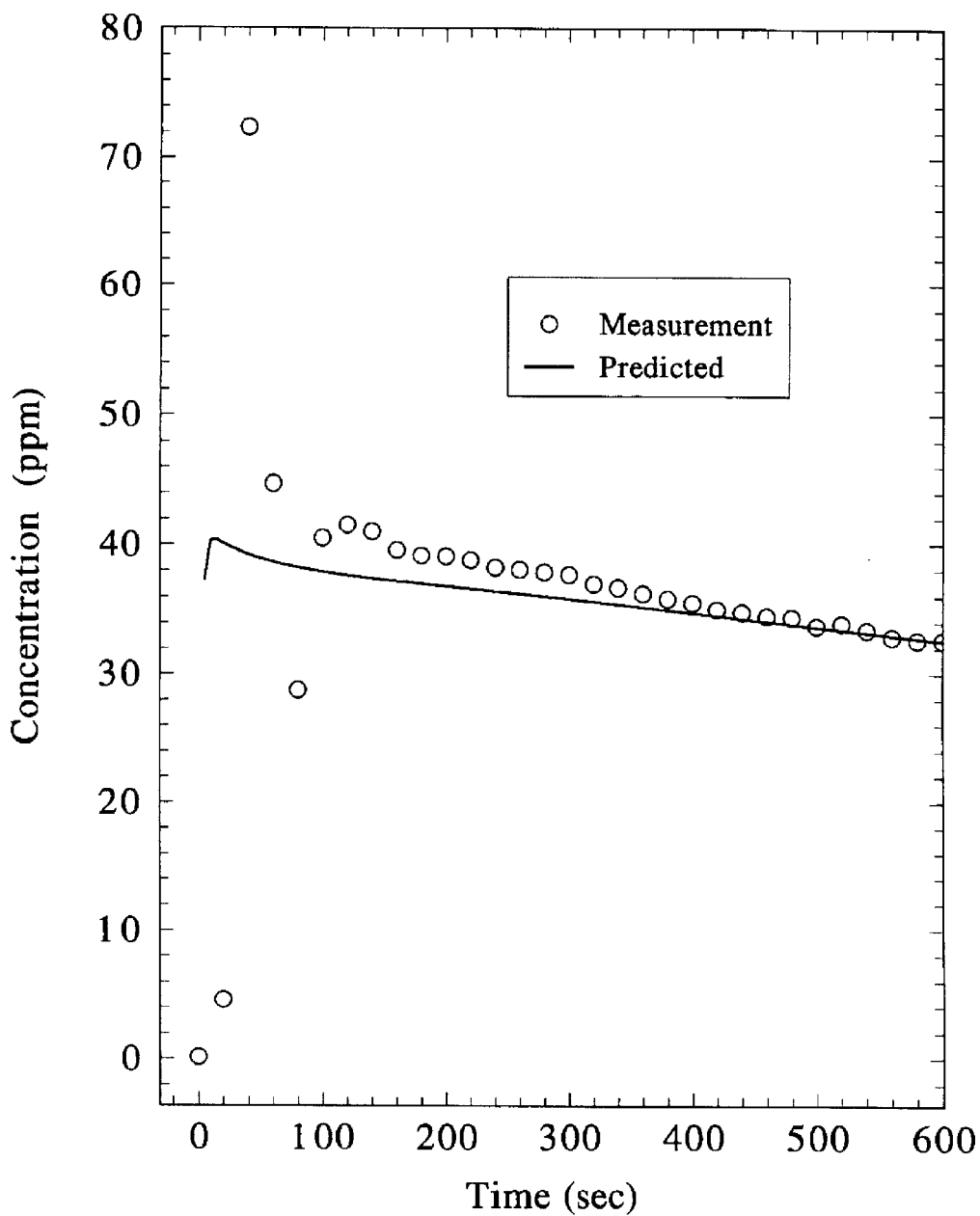
Figure 11:
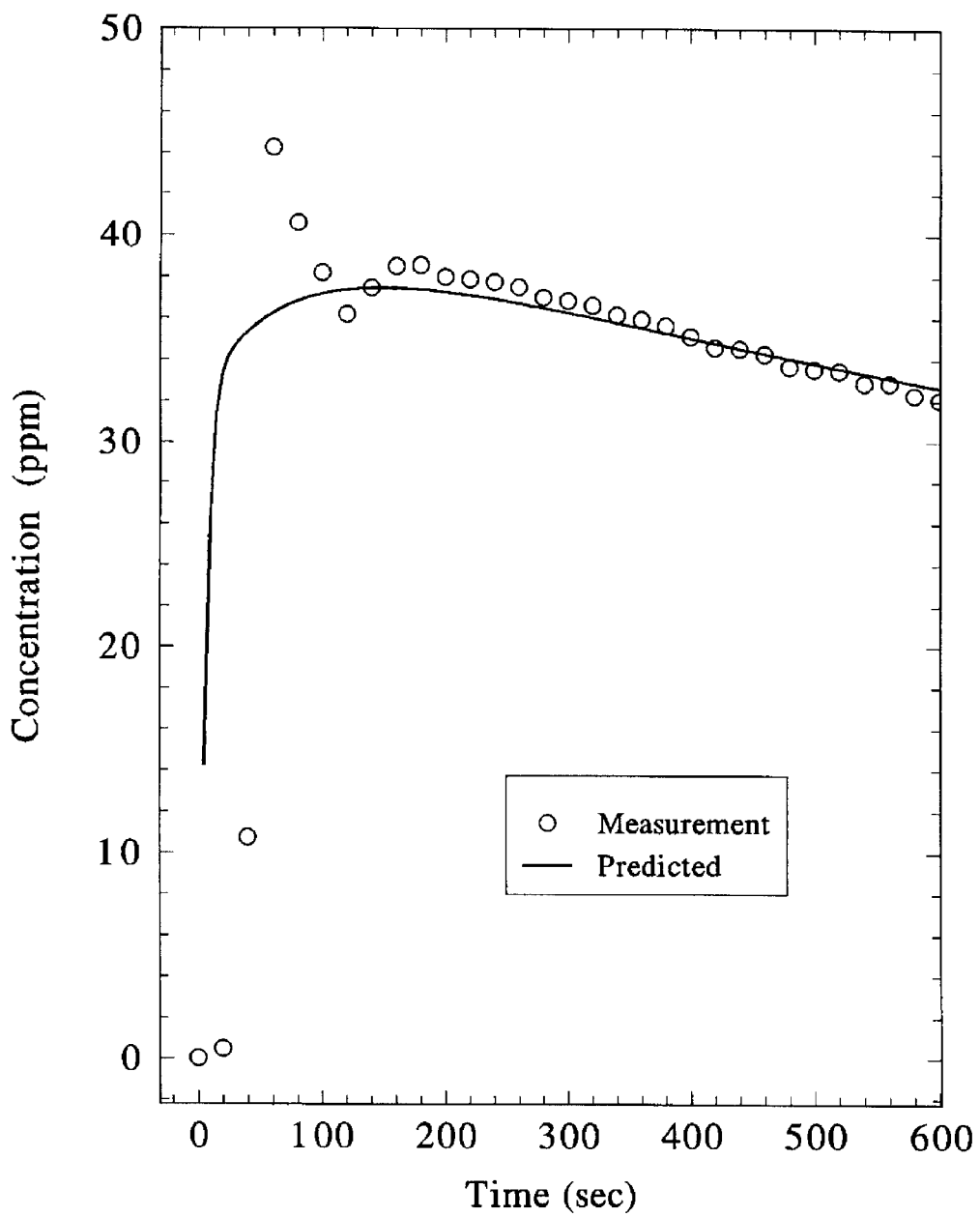
FIG. 11 is a graph comparing predicted and measured concentrations in Room 2.2b.
Figure 12:
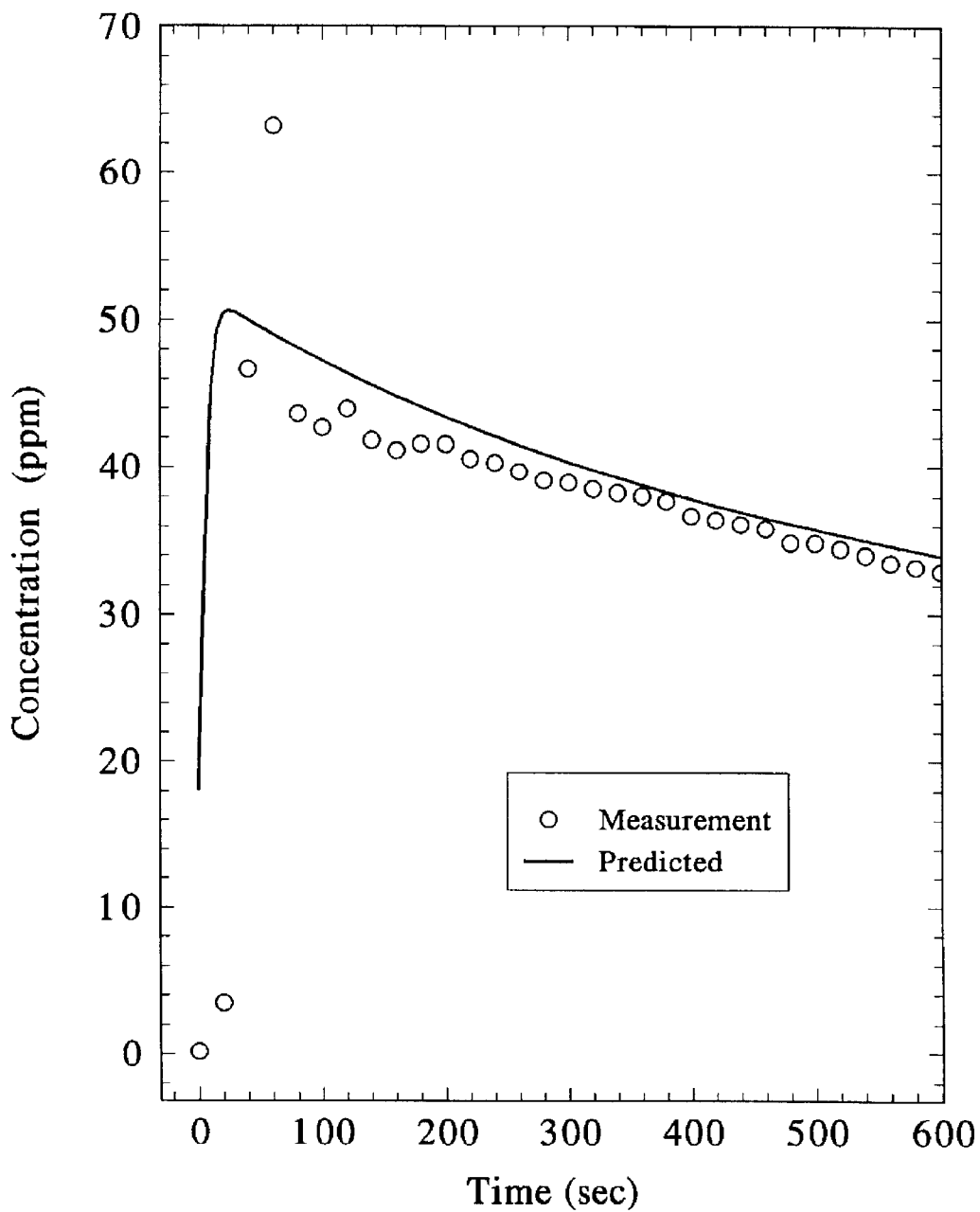
FIG. 12 is a graph comparing predicted and measured concentrations in Room 2.3.
Figure 13:
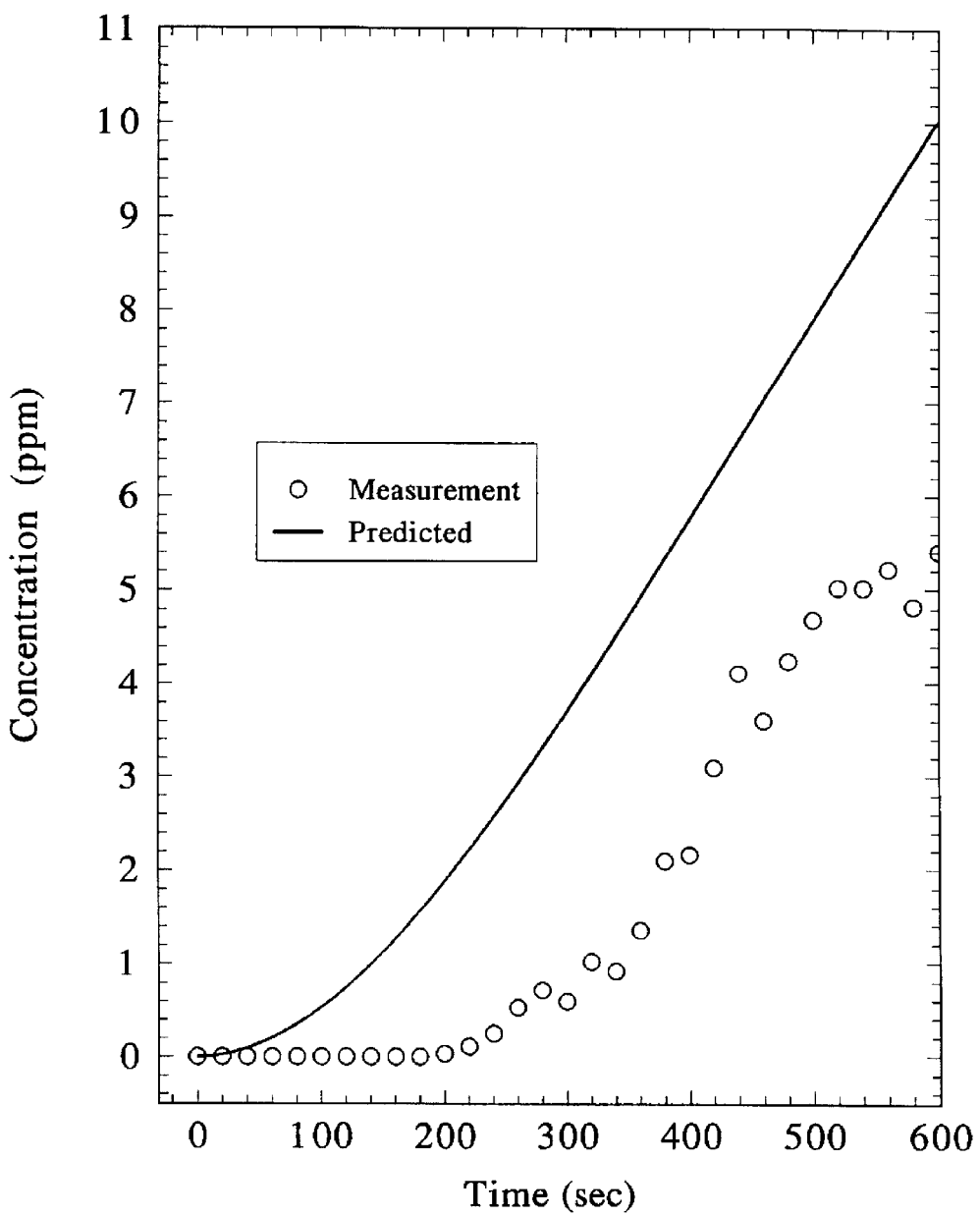
FIG. 13 is a graph comparing predicted and measured concentrations in Attic.
Figure 14:
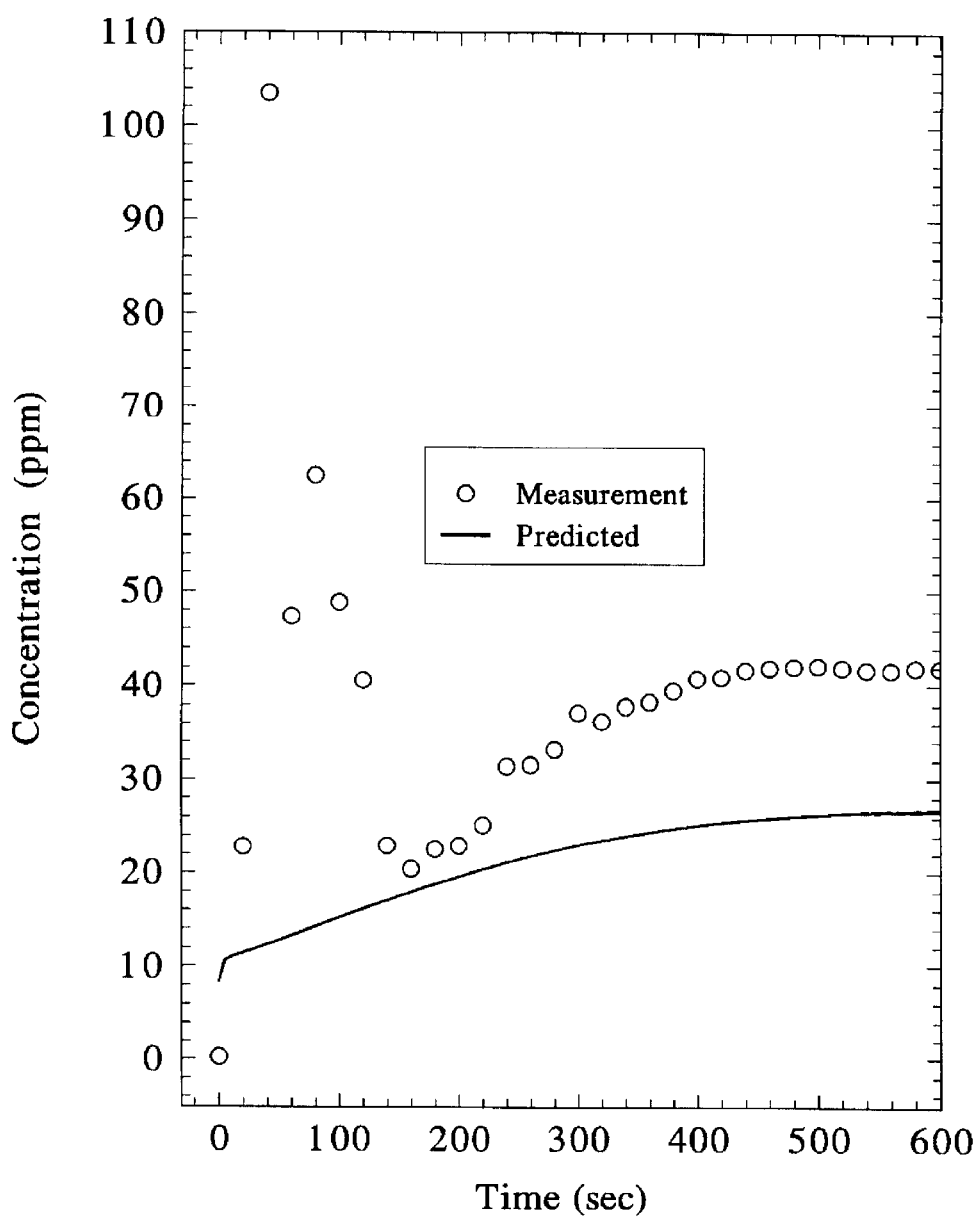
FIG. 14 is a graph comparing predicted and measured concentrations in Stairs 1.
Figure 15:
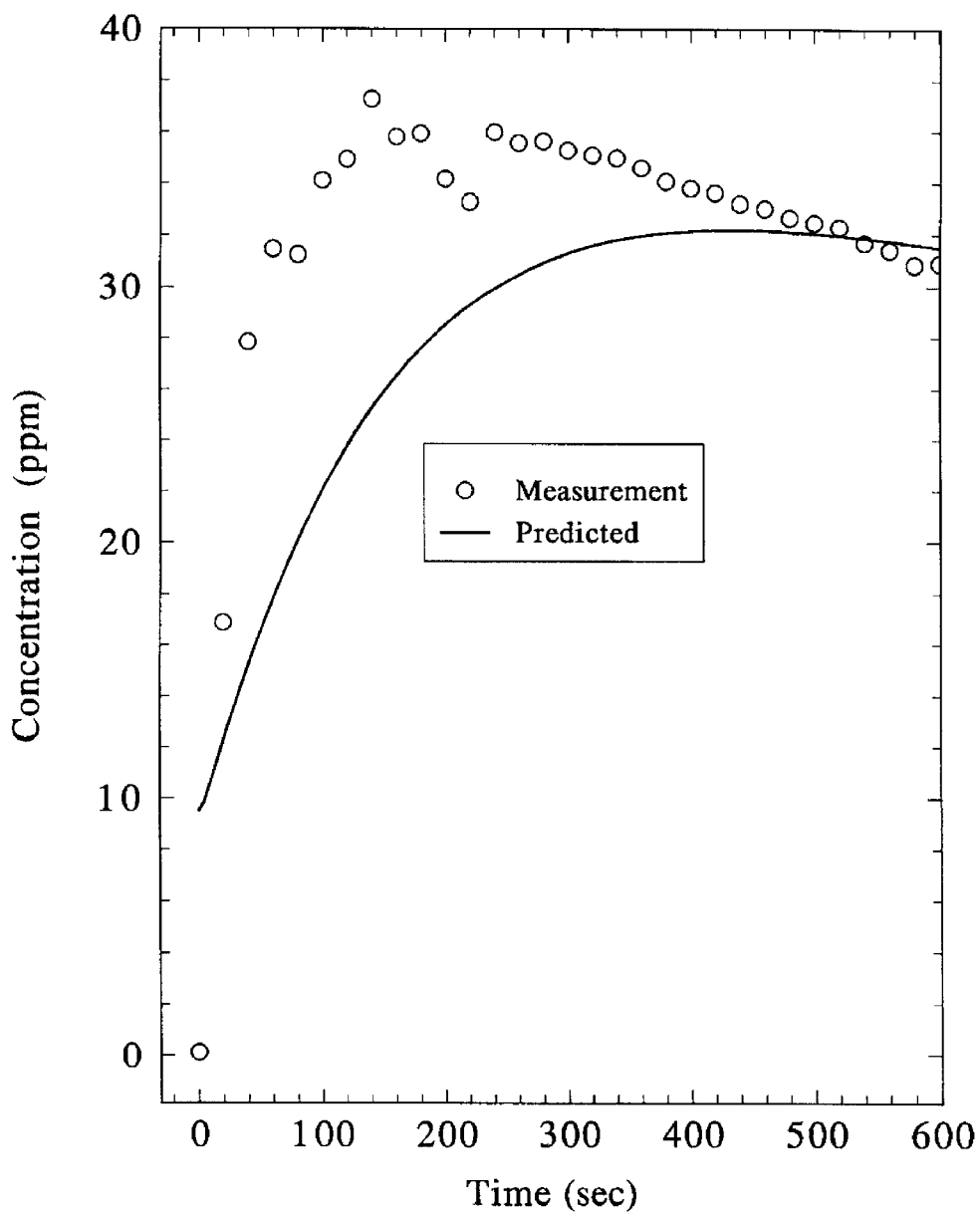
Figure 16:
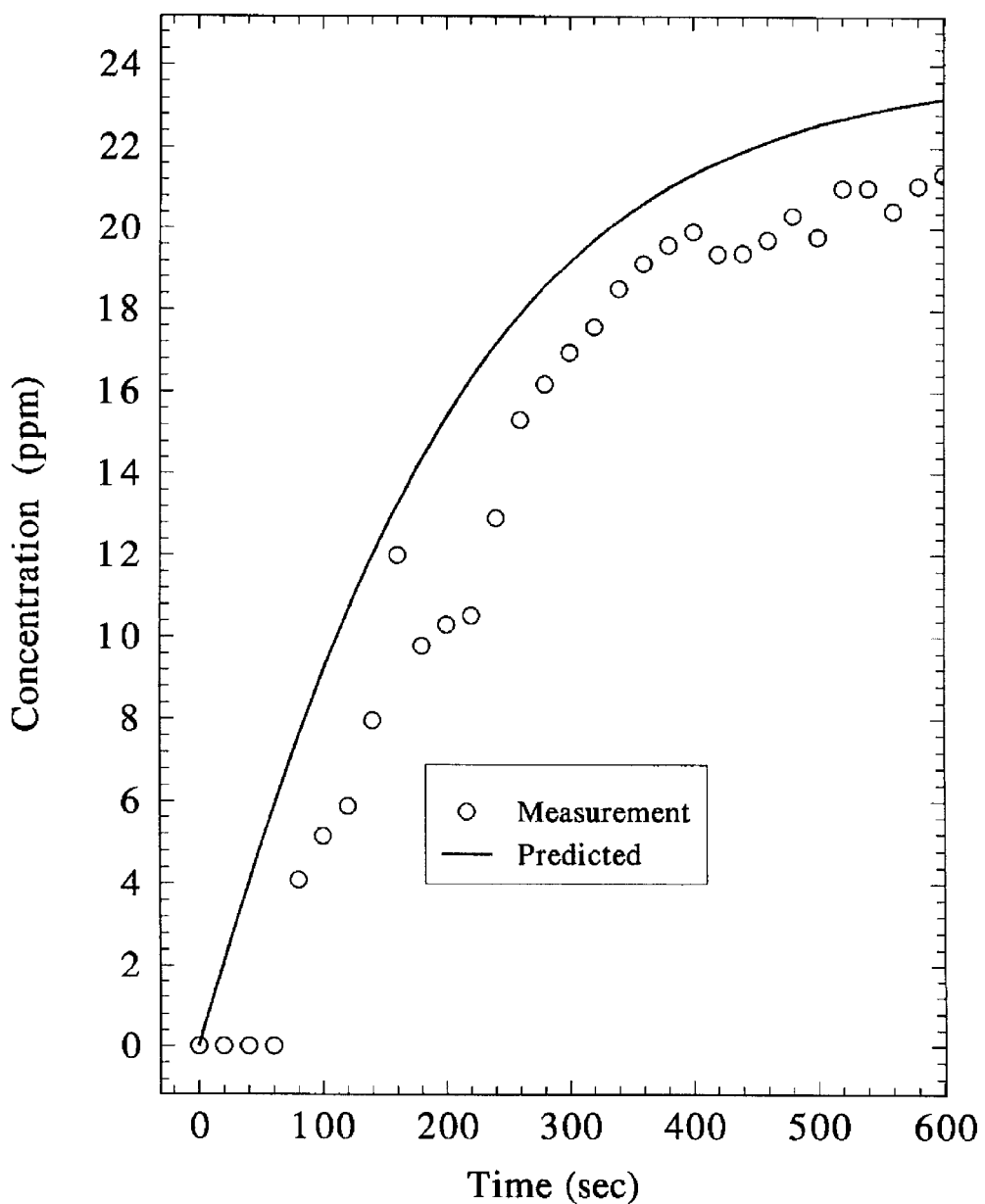
FIG. 16 is a graph comparing predicted and measured concentrations in Stairs 3.

The German Village Inn located at the Dugway Proving Grounds in Utah was selected for simulated toxic agent dispersal studies in a building. The Inn is a three-story apartment building, with six apartments. The middle southern apartment was selected for the experiments. As shown in FIGS. 2 and 3, the first and second floors have three rooms each. The third floor is a single room attic, and an open stairwell joins the three floors. One large room on the first floor was partitioned into two rooms by a temporary wall. The doorway in this temporary wall remained opened for the test. The second floor had the same floor plan as the first floor, but without the temporary wall. The attic was modeled as one cell, and the three stairwells were modeled with one cell each. The first floor was modeled with one cell per room. The second floor was modeled with four cells, two of which were used for the large room. Thus a total of twelve cells were used for the rooms and stairwells. An additional eight cells were used for the air ducts. Airflow rates and leakage rates to the outside were provided as part of the experiment. All doors in the building were open, except the first floor door to the outside. The HVAC (Heating Ventilation and Air Conditioning) system was running throughout experiment to each room. The airflow interconnectivity among the computational cells is shown in FIG. 4. Propylene sensors were placed in each of the twelve cells at a height of 5 ft. The details of the building and test conditions are reported in United States Department of Defense, "911-Bio Consequence Management ACTD Final Report" (1998).

To test the present invention the Oct. 21, 1997, 911-Bio-ACTD German Village Exercise number GV1 was simulated. In this exercise approximately 34.5 grams of propylene gas contained in two balloons with a total volume 22.3 liters was released in the HVAC return vent of Room 1.2a shown in FIG. 2.

The present invention was tested by blindly predicting sensor readings in one room from readings in other rooms. Eleven sensors for twenty cells were used to predict concentrations in one cell. However, the eleven sensors were not placed (i.e., distributed) in near-optimal locations prior to running the experiment by using the method of the present invention to determine near-optimal placements.

FIGS. 5 to 16 show the results for blind predictions in the twelve rooms, respectively. The predictions are shown as solid lines and the circles represent the measured data. Except for Room 1.1 shown in FIG. 5, and Stairwell 1 shown in FIG. 14, the predictions agree very well with the measurements even when the data are noisy such as for Rooms 1.2a and 1.3, in FIGS. 6 and 8, respectively. Considering that there are no adjustable parameters in the calculations, the overall agreement with the measurements is very good.

EXAMPLE 2

Figure 17:
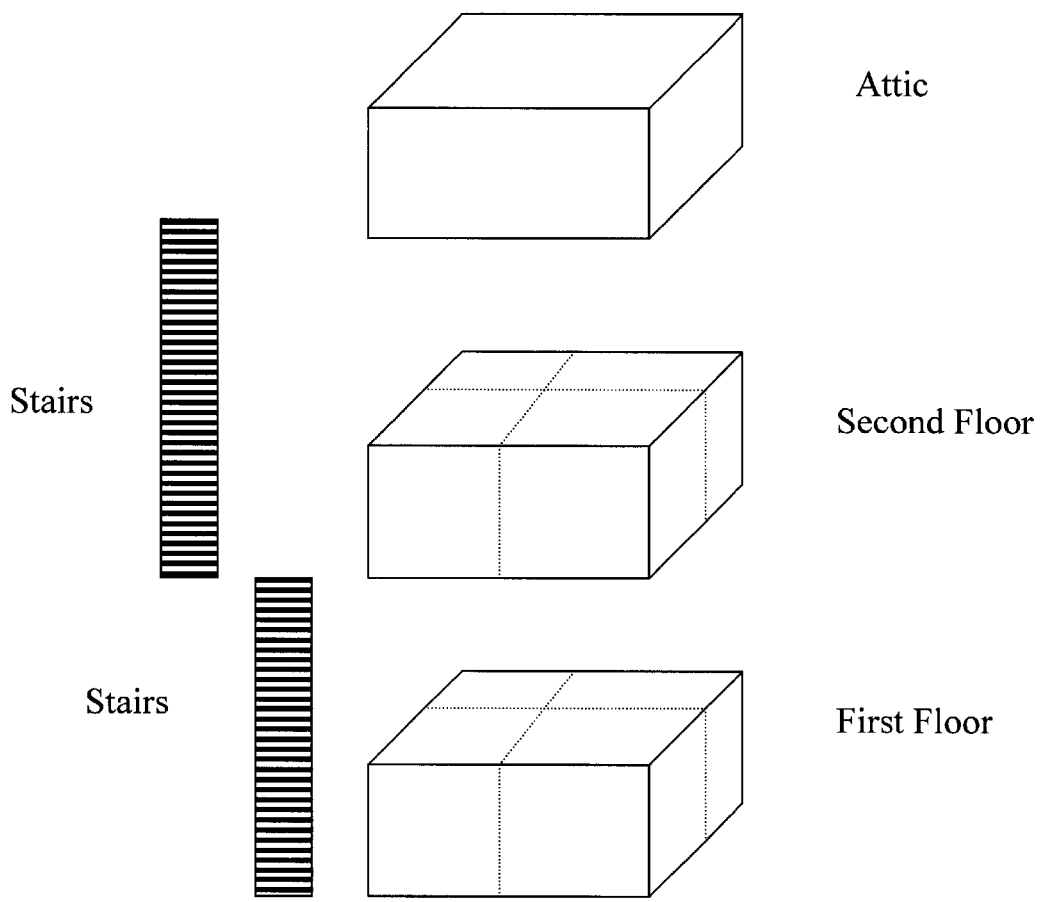
FIG. 17 is a schematic representation of the "German Village" structure.
Figure 18:
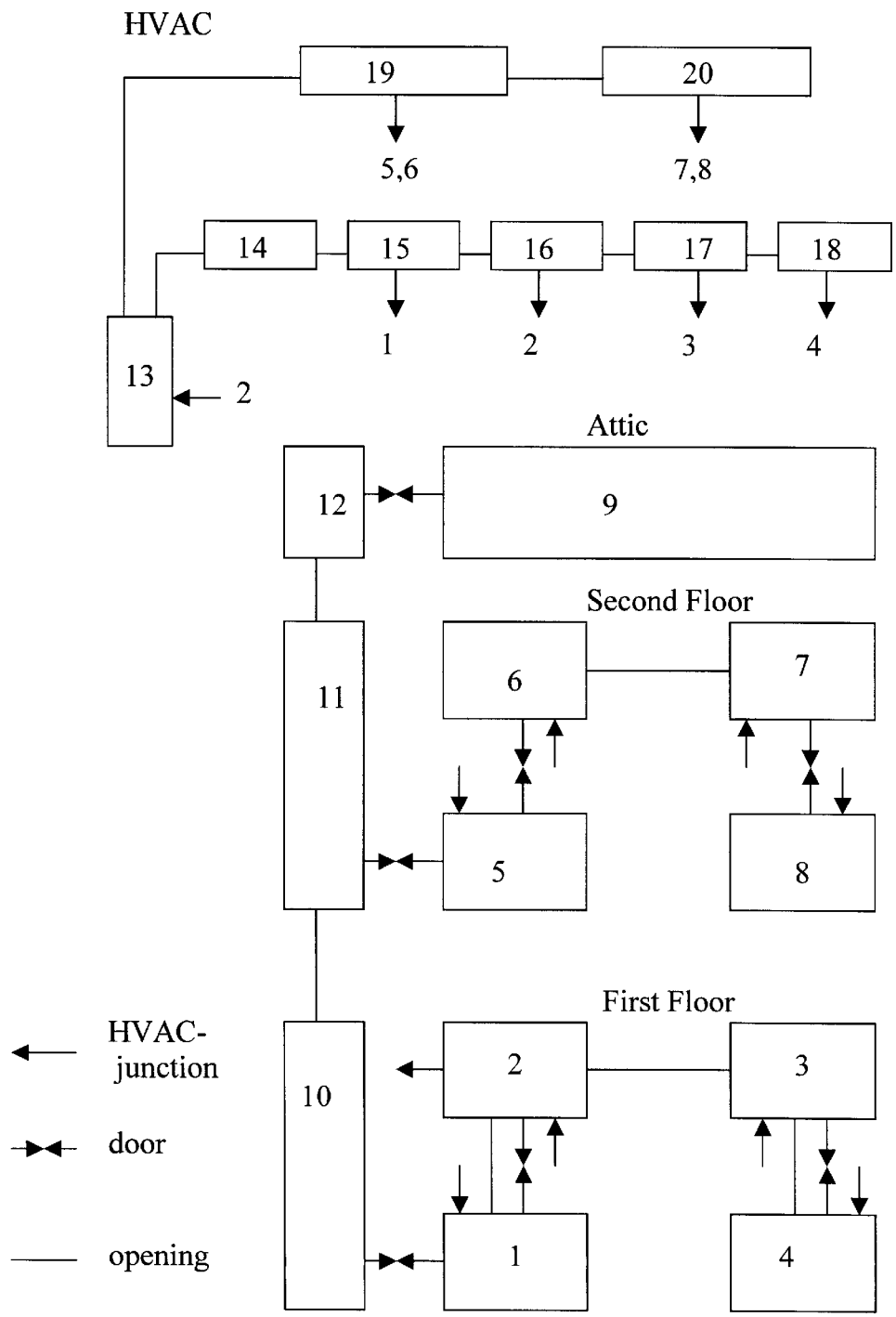
FIG. 18 is an alternate flow interconnectivity diagram of the "German Village" structure.

The search method of the invention was also employed with the flow matrix data for the German Village experiments. The flow matrix data were determined using the CONTAIN code (Murata, K. K., et al., "Code Manual for CONTAIN 2.0: A Computer Code for Nuclear Reactor Containment Analysis," Vol. I, Rep. NUREG/CR-6533, Sandia National Laboratories, Albuquerque, N.Mex., SAND97-1735 (1997)). As shown schematically in FIG. 17, the test facility consisted of a two-story apartment with an attic and two sets of stairs. The first two floors were partitioned into rooms, and the HVAC (Heating, Ventilation and Air Conditioning) system was operating when a contaminant was released into one room on the first floor. For modeling purposes, the rooms, attic, stairs, and HVAC are approximated with a total of 20 well-mixed cells. The interconnectivity among the cells and the cell numbering are shown in FIG. 18. In the actual test, 12 sensors were placed inside cells 1 through 12. To demonstrate the advantages of the near-optimal sensor placement distribution, calculations will be based on only 8 sensors and 6 sensors. After 100 seconds of sampling, the contaminant concentrations throughout the building must be determined in our calculations for the next 300 seconds from these limited data. During the actual test, gas samples were taken every 20 seconds. By using the same sampling frequency in our calculations, only 6 samples are obtained for each sensor before a prediction is made for the entire facility.

Because no data are available that provide contaminant concentrations for all 20 cells, a synthetic data set was prepared by calculating the concentrations in all cells for a release in cell 2 that would result in an initial concentration, $C_{initial}$, in cell 2 of 1000 mg/m³. The concentrations in all cells for 400 seconds of simulation were then stored as synthetic data. To simulate actual measurements, a random noise factor of ±50% was incorporated to each concentration in the synthetic data set.

Figure 19:
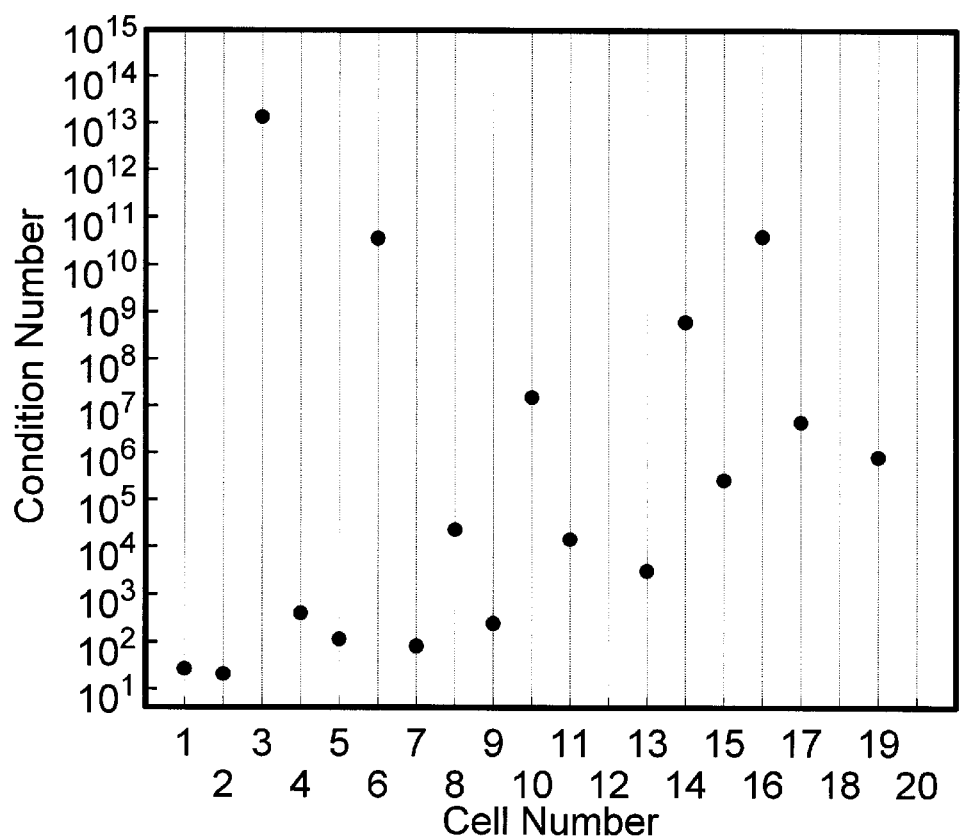
FIG. 19 is a chart of the system-sensor matrix condition number for Example 2.
Figure 20:
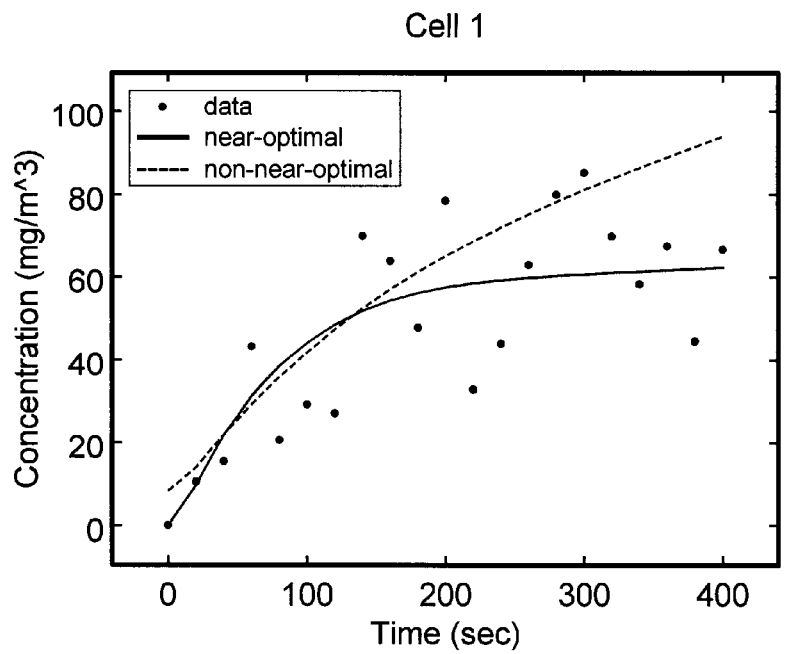
FIGS. 20–31 are comparisons of predictions using 8 sensors for near-optimal and non-near-optimal distributions for Cells 1–12, respectively.

The increase in the condition number as sensors are removed from the distribution is shown in FIG. 19. The plotted condition numbers are for the removal of sensors in the cells given on the x-axis, that resulted in the smallest increase in the condition number with the resulting condition number shown on the y-axis, given that sensors have already been removed from cells with smaller condition numbers plotted in FIG. 19. A vertical line is drawn for each cell so that the cell number can be more easily read from the x-axis. For the first sequence, removing the sensor in cell 2 has the smallest increase in the condition number. For the next sequence, removing the sensor in cell 1 has the smallest increase in condition number. If the one-sensor-at-a-time search algorithm is continued until 12 sensors are removed, then for the near-optimal sensor placement distribution the remaining sensors are in cells 3, 6, 10, 12, 14,.16, 18, and 20. As can be seen from FIG. 19, by retaining sensors in these cells the system-sensor matrix condition number is less than $10^7$. (The condition number for cells 12, 18, and 20 are not shown in FIG. (19) because the value is larger than $10^{15}$.) The computation time on a 200 MHz PC was less than 10 seconds to determine the near-optimal placement of 8 sensors in 20 cells. From Eq. (20), the computations required the evaluation of 306 sensor placement distributions.

As an example of a non-near-optimal distribution, sensors were placed in cells 1, 2, 4, 5, 7, 8, 9, and 11. This sensor placement distribution intentionally does not have a sensor in any cell that has a sensor for the near-optimal distribution. As can be seen in FIG. 18, the room and stairway cells are numbered 1 to 12. Thus, the non-near-optimal distribution is also consistent with the original test procedure in which sensors were only placed in rooms and stairways, and not in the HVAC. The non-near-optimal choice should be favored by this computational experiment because a sensor is in the same room as the initial release. However, because the condition number for the non-near-optimal distribution is $1.6 \times 10^{12}$, (which is much larger than that for the near-optimal distribution), the near-optimal sensor placement strategy stills give a better prediction of contaminant concentrations throughout the building (as will be shown below).

To quantitatively evaluate the two predictions, we define the prediction error as $$\varepsilon = \sum_{i=1}^{N_t} \sum_{j=1}^{N_c} \left[ \frac{C_{i,j,inv} - C_{i,j,ex}}{C_{initial}} \right]^2 \tag{21}$$

$C_{i,j,inv}$=concentration in cell i at time j calculated by the inverse algorithm,
$C_{i,ex}$=concentration in cell i at time j for the synthetic data without noise,
$C_{initial}$=initial concentration of release (1000 mg/m³ for this example), and
$N_t$=number of samples per sensor for 400 seconds (21 for this example).
Because $C_{i \neq 2,1,ex}$ is zero, use $C_{initial}$ to normalize the difference between the calculated and exact concentrations in Eq. (21). This normalization also has the advantage that high concentration errors are weighted more heavily for assessing the prediction errors.

Figure 21:
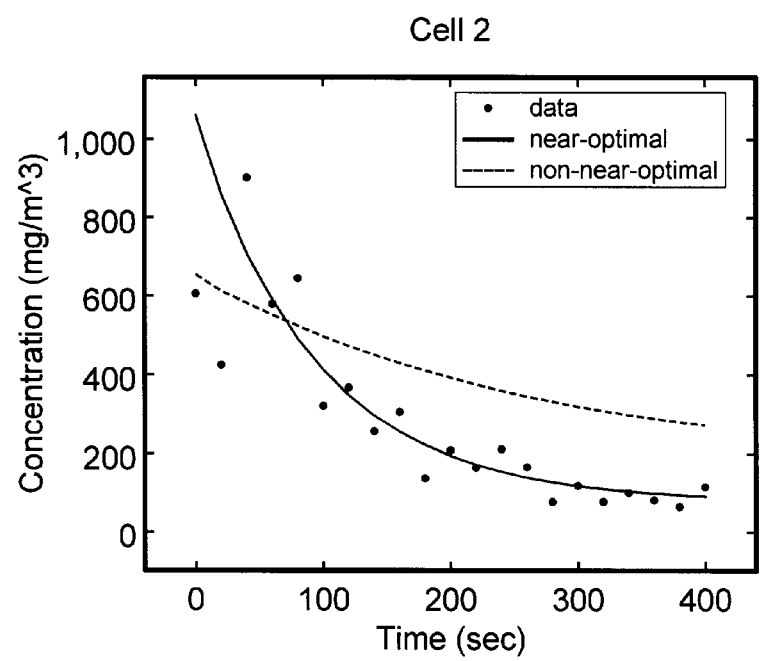
Figure 22:
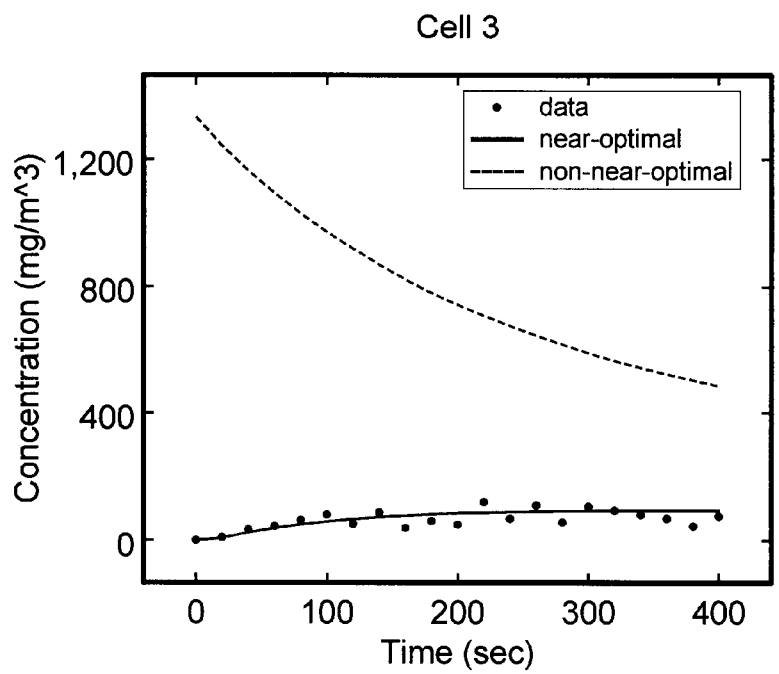
Figure 23:
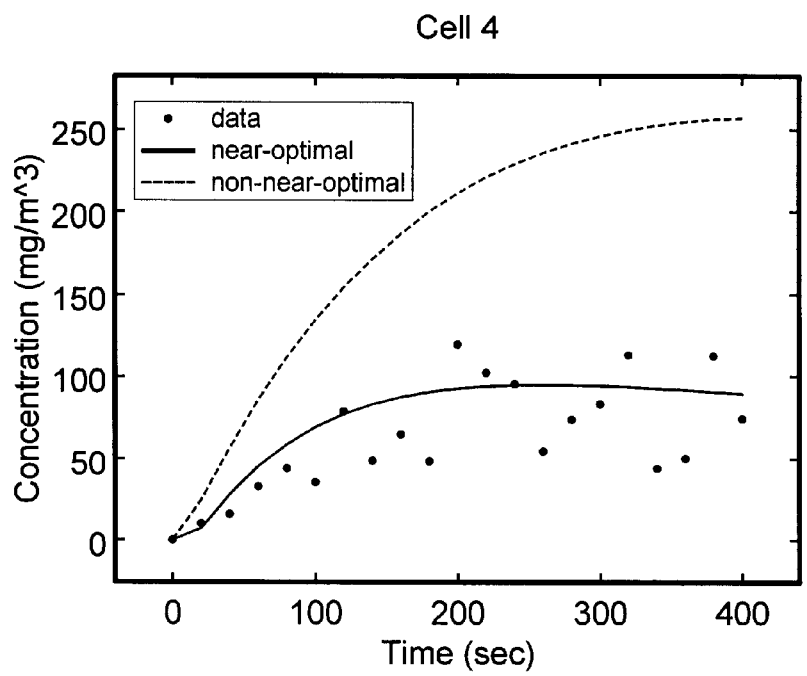
Figure 24:
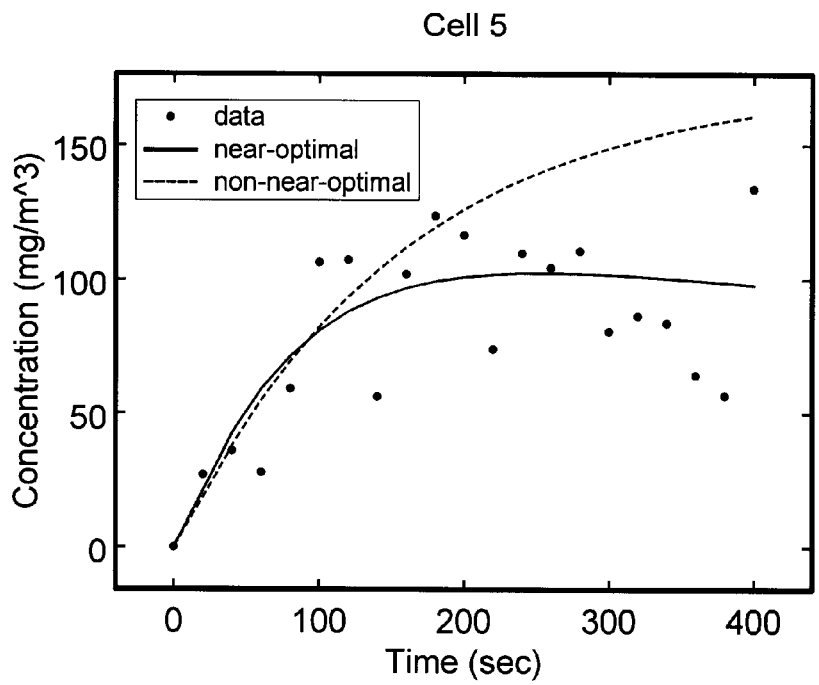
Figure 25:
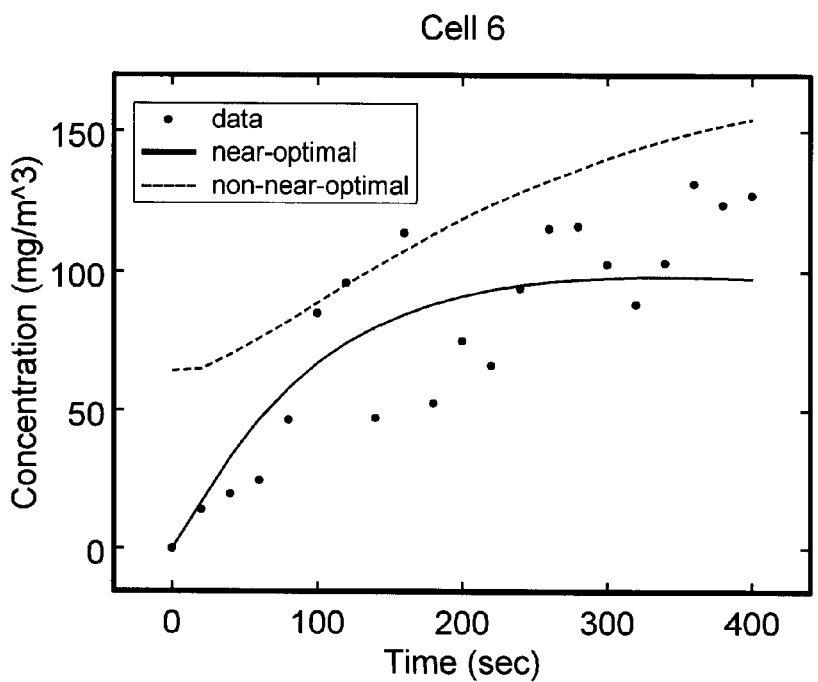
Figure 26:
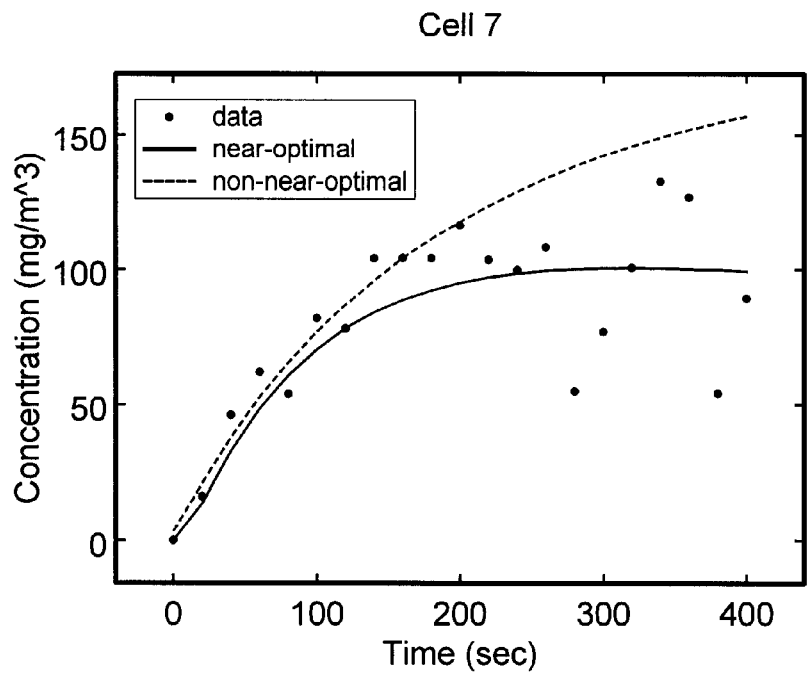
Figure 27:
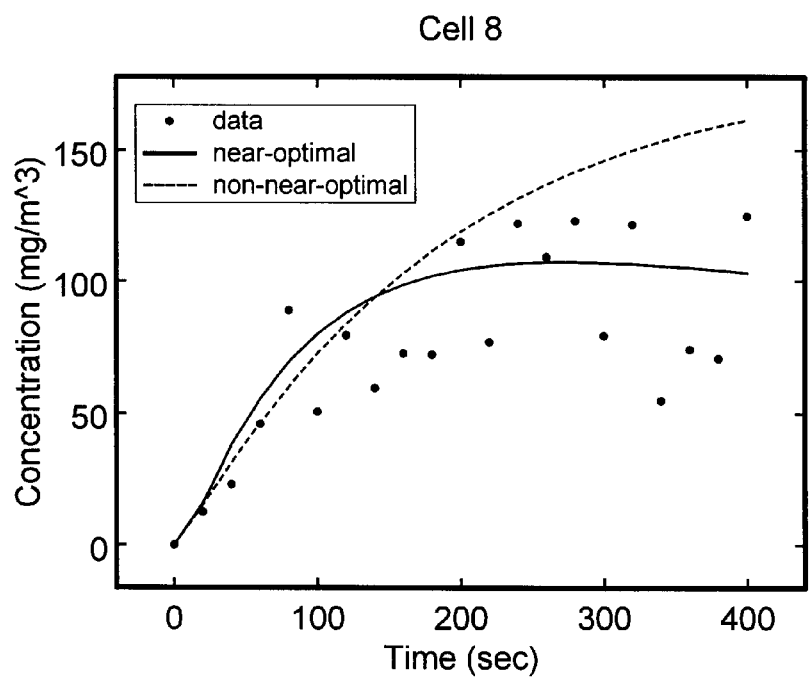
Figure 28:
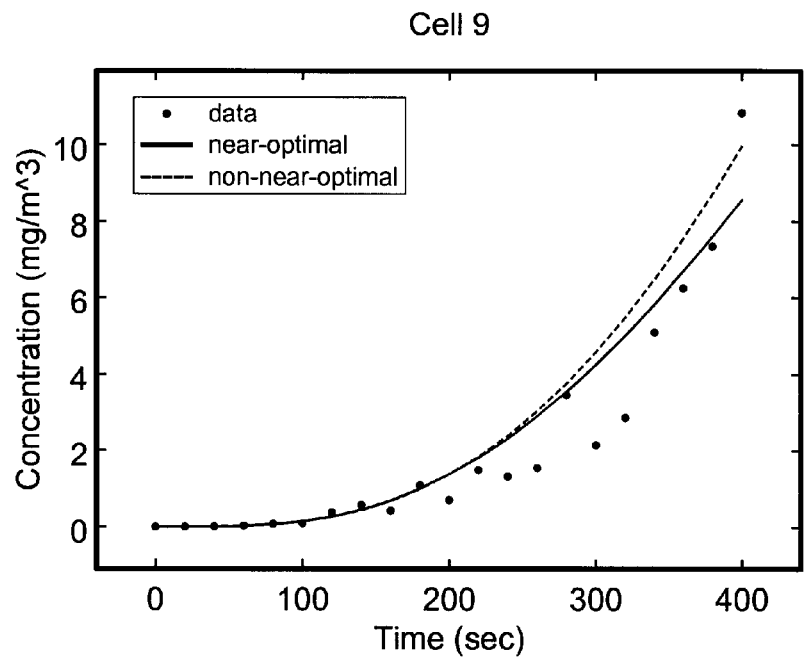
Figure 29:
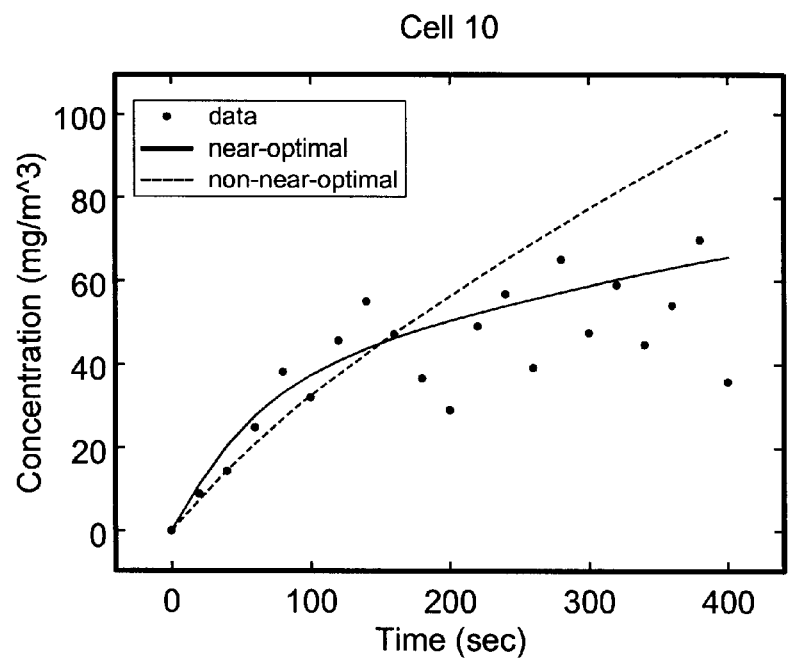
Figure 30:
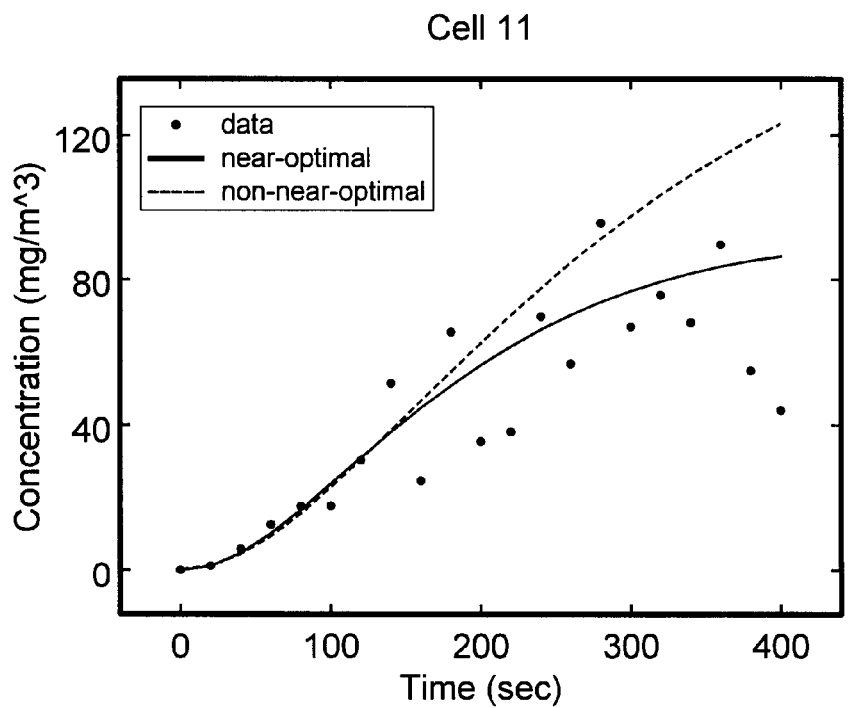
Figure 31:
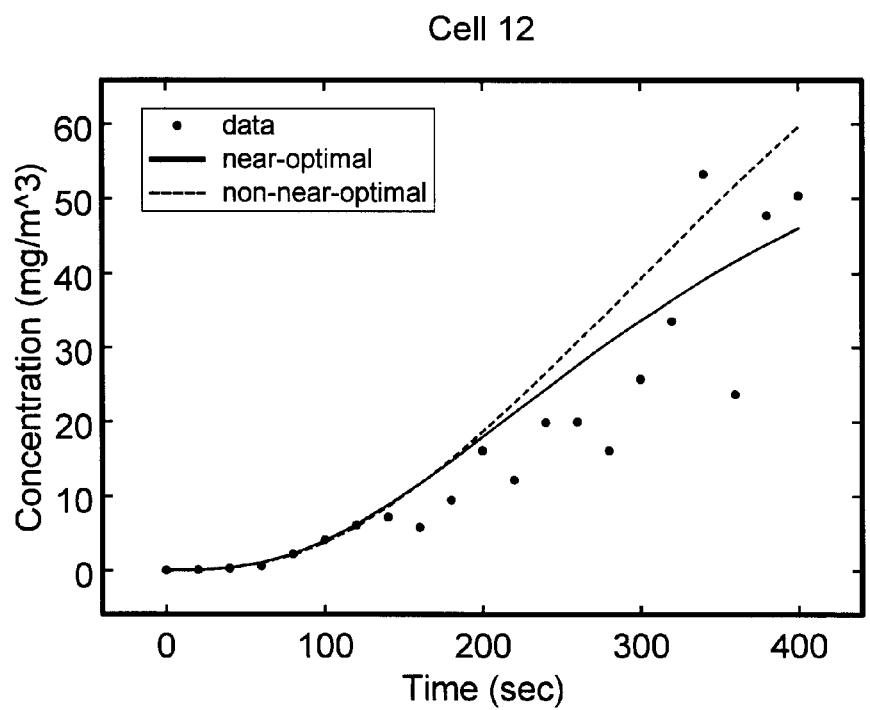
Figure 32:
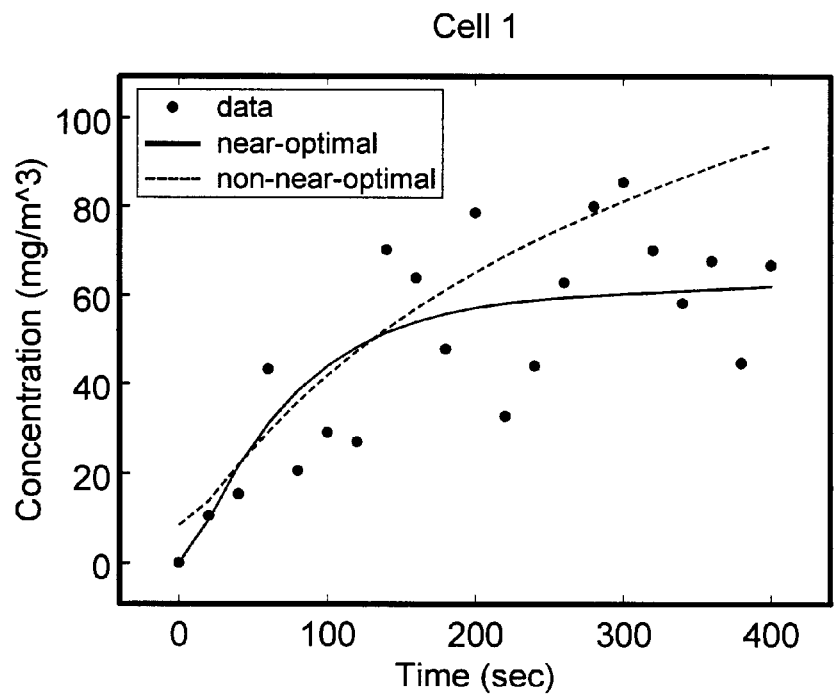
FIGS. 32–43 are comparisons of predictions using 6 sensors for near-optimal and non-near-optimal distributions for Cells 1–12, respectively.
Figure 33:
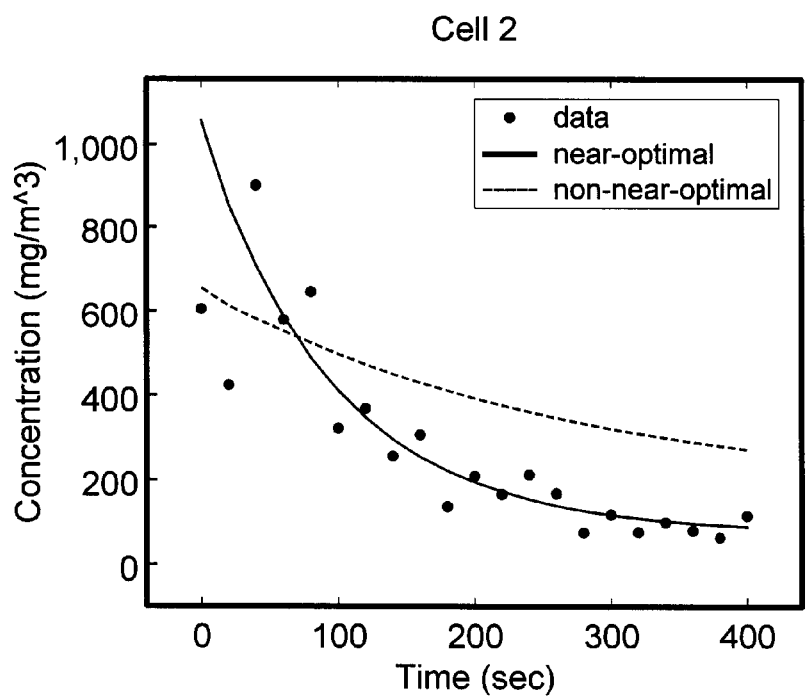
Figure 34:
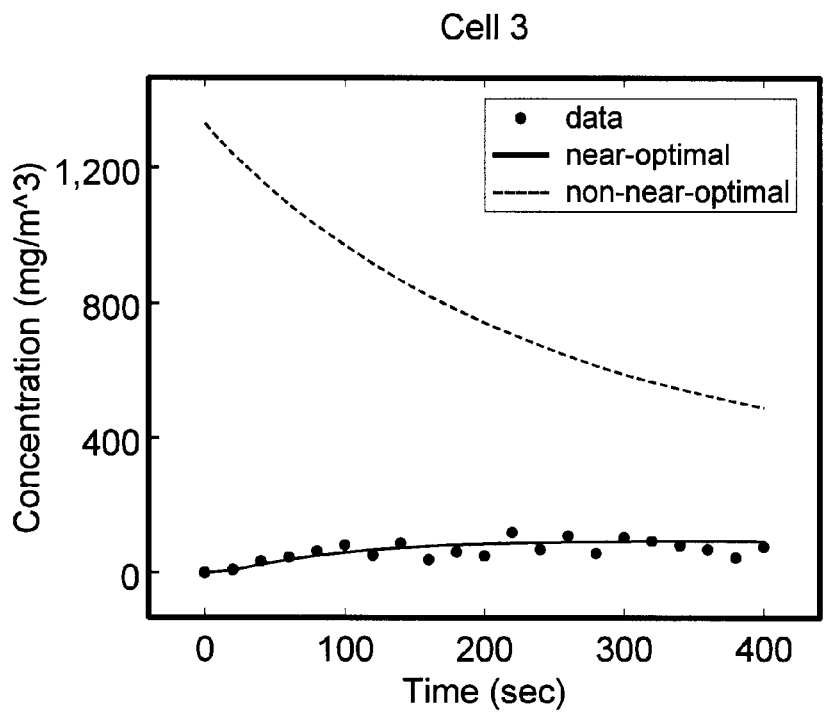
Figure 35:
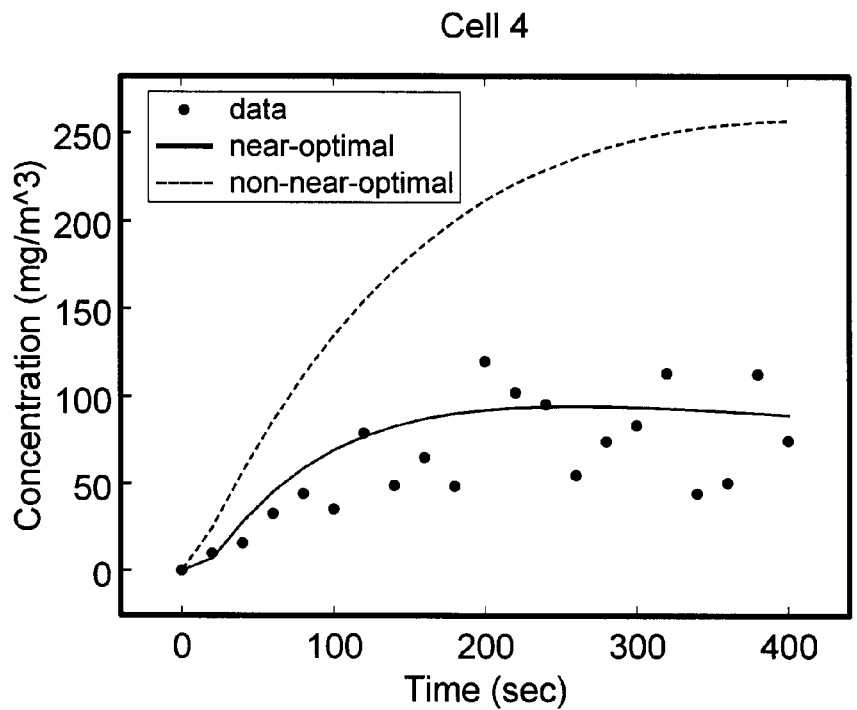
Figure 36:
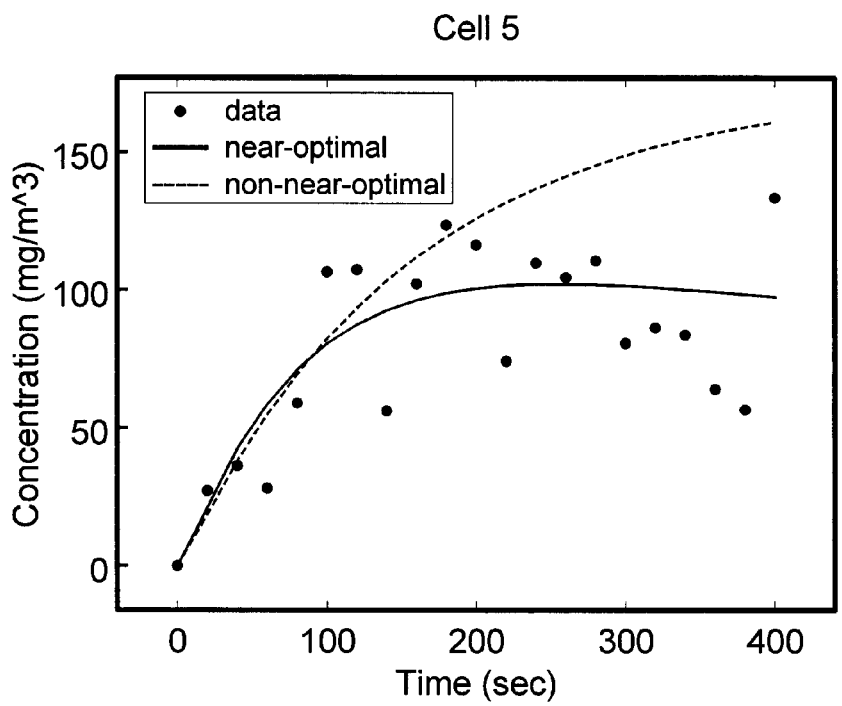
Figure 37:
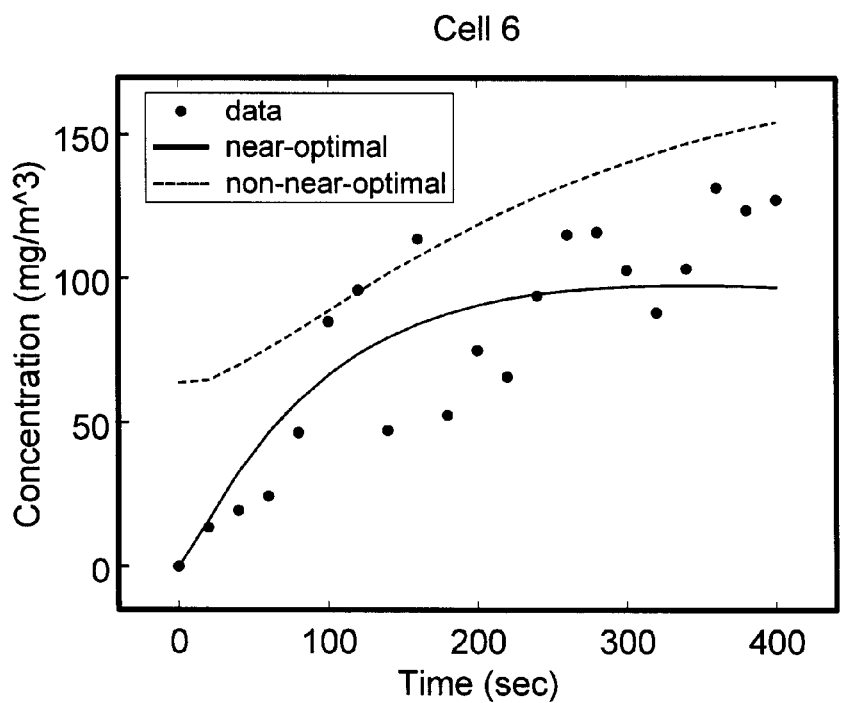
Figure 38:
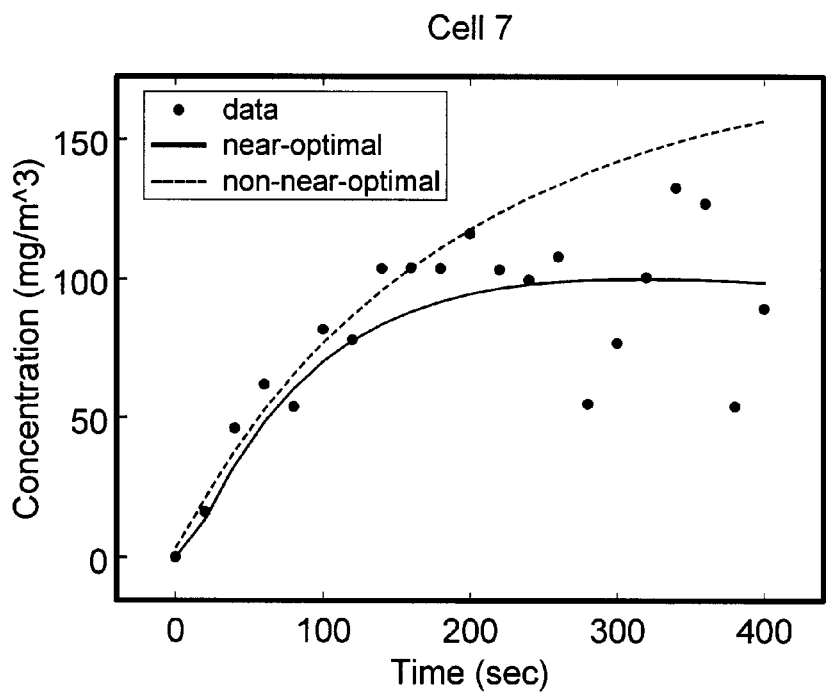
Figure 39:
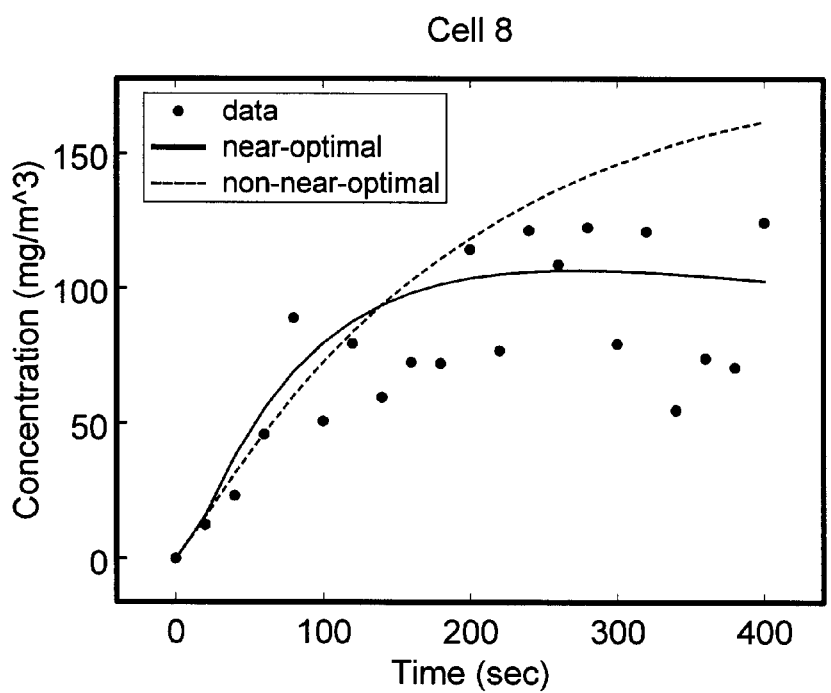
Figure 40:
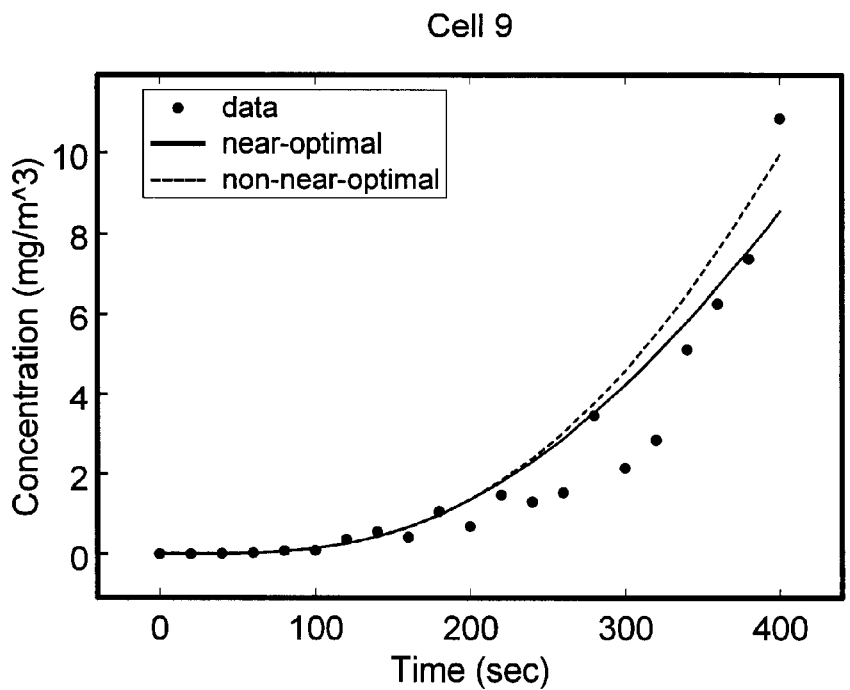
Figure 41:
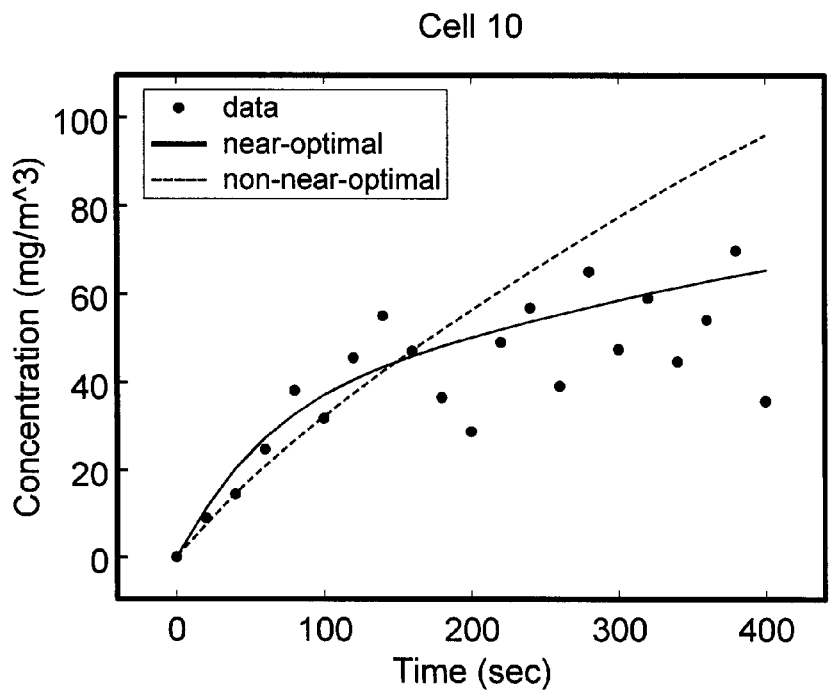
Figure 42:
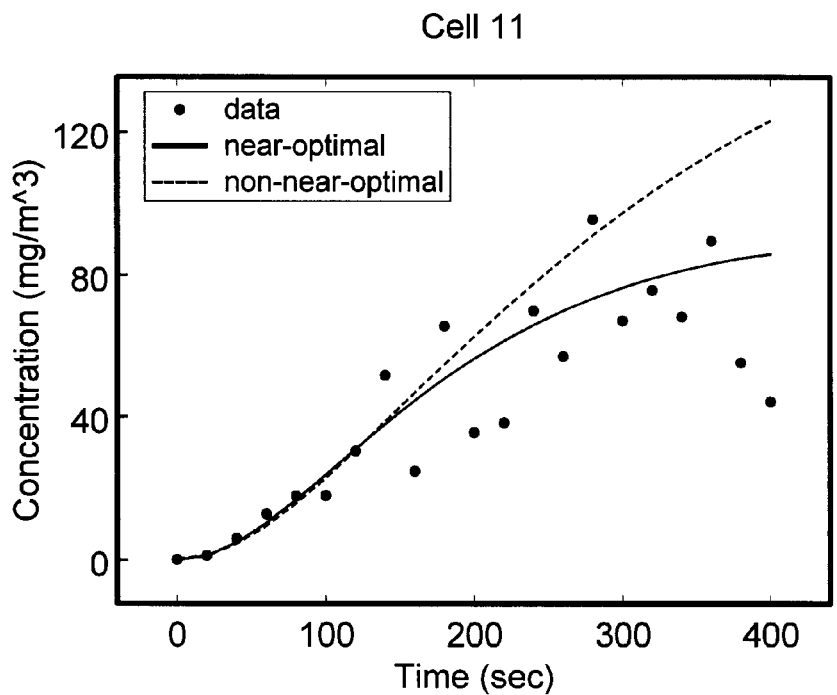
Figure 43:
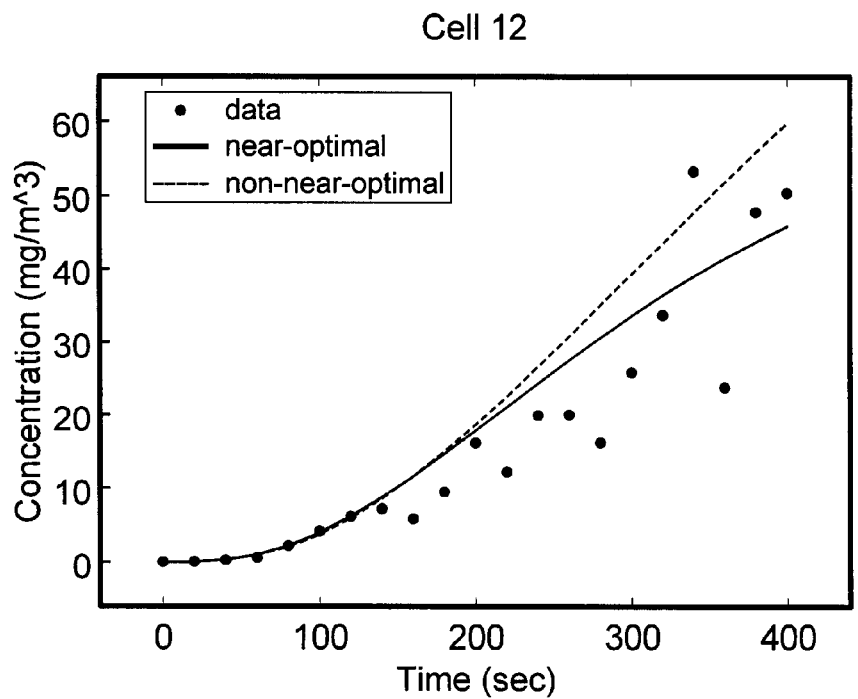

The predicted concentrations for the near-optimal and non-near-optimal sensor distributions in the first 12 cells are shown in FIGS. 20 to 31, as solid and broken lines, respectively. The noisy data are shown as discrete points. Notice that in all cases the near-optimal distribution has better agreement with the data. In particular, as shown in FIGS. 21 and 23 for cells 2 and 4, respectively, the near-optimal predictions are far better even though no sensors are in these cells for this distribution, but are in these cells for the non-near-optimal distribution.

From FIG. 19 one sees that the condition number increases significantly if a sensor is removed from cell 3. Thus, for the near-optimal distribution there is a sensor in this cell, and for comparison the non-near-optimal distribution does not have a sensor in this cell. In FIG. 22 one sees the dramatically better agreement with data when a sensor is in cell 3, which supports the importance of using a search method for locating sensors.

Finally, the error as defined by Eq. (21) for the non-near-optimal and near-optimal distributions are 14.1 and 0.0151, respectively. Thus, the near-optimal distribution reduced the error by approximately three orders of magnitude, for the same number of sensors, even though no sensor was in the cell from which the release occurred.

To further test the near-optimal search method of the invention, only 6 sensors were used for the same experiment. From FIG. 19, the near-optimal locations of the six sensors (corresponding to the six highest condition numbers) are cells 3, 6, 12, 16, 18, and 20. If sensors remain only in these cells, the condition number is $6.2 \times 10^8$. This condition number is low enough that one can still expect an accurate determination of the initial concentrations, and hence accurate predicted concentrations. The predicted concentrations in cells 1 to 12 are shown in FIGS. 32 to 43 when using these 6 cells with the same noisy data for 100 seconds providing the basis for the predictions. Also shown in these Figures are the noisy data and the non-near-optimal concentrations predicted using 8 cells. Notice that in all cases the near-optimal distribution predictions are better than the non-near-optimal distribution predictions, even though more sensors are used for the non-near-optimal distribution. The error for the near-optimal distribution as given by Eq. (21) for 6 sensors is 0.0127, which is comparable to that obtained with 8 sensors in a near-optimal distribution. The predictions with the near-optimal distribution were very similar using either 6 or 8 sensors.

The method was demonstrated by using synthesized noisy data for release in one room of the German Village facility. In this computational experiment, measurements in 8 or 6 cells using the near-optimal placement distribution were taken for 100 seconds, and predictions were made for all 20 cells in the facility for the next 300 seconds. Excellent predictions were obtained if sensors were near-optimally distributed, even though no sensor was located in the cell where the release occurred. Far less accurate predictions were obtained with a non-near-optimal sensor placement distribution using 8 sensors, even though two more sensors were used, and a sensor was located in the cell where the release occurred.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of inferring airborne contaminant concentrations in interconnected rooms without sensors from data collected by sensors located in other interconnected rooms of a building, the method comprising:

receiving airflow interconnectivity data for the building;

receiving measured contaminant concentration data from contaminant sensors in the building; and inferring contaminant concentration data for rooms without sensors from the flow interconnectivity data and the measured contaminant concentration data.

2. The method of claim 1 wherein the inferring step occurs substantially in real time when the receiving contaminant concentration data step occurs substantially in real time.

3. The method of claim 1 wherein the inferring step comprises solving a least squares problem.

4. The method of claim 3 wherein solving a least squares problem comprises minimizing a difference between measured and predicted contaminant sensor concentrations with respect to an unknown contaminant release time.

5. The method of claim 4 wherein the minimizing step comprises constraining the solutions to provide non-negative initial contaminant concentrations in all rooms.

6. The method of claim 1 additionally comprising the step of inferring one or more contaminant initial release points from the received and the inferred concentration data.

7. The method of claim 1 additionally comprising the step of providing the measured and the inferred concentration data to a system capable of determining and communicating preferred escape routes to personnel in the building.

8. The method of claim 1, wherein the number of sensors can vary with time during the collection of data by the sensors.

9. The method of claim 1, wherein the airflow between interconnected rooms can vary piecewise with time.

10. The method of claim 1, wherein receiving measured contaminant concentration data from contaminant sensors in the building comprises receiving time-dependent measured contaminant concentration data.

11. A method of determining a near-optimal distribution of contaminant sensors in rooms of a building, wherein the number of contaminant sensors is less than the number of rooms in the building, comprising determining a sensor placement distribution having a system-sensor matrix, M, that is non-singular.

12. A method of determining a near-optimal distribution of contaminant sensors in rooms of a building wherein the number of contaminant sensors is less than the number of rooms in the building, comprising determining a sensor placement distribution having a system-sensor matrix, M, that is non-singular, wherein determining the sensor placement distribution comprises determining a sensor placement distribution having the lowest condition number of all sensor placement distributions considered.

13. The method of claim 12, wherein the lowest condition number of the sensor placement distributions considered is less than or equal to a near-optimality criterion.

14. The method of claim 12, wherein the near-optimality condition number criterion is approximately less than or equal to $10^9$ for computations in double precision.

15. The method of claim 12, wherein the near-optimality condition number criterion is such that machine round-off error is unimportant.

16. The method of claim 12, further comprising:

a) initially assuming that the number of sensors, $N_{test}$ equals the number of rooms in the building;

b) temporarily removing a sensor from a room that has not previously had its sensor removed, then calculating and storing the condition number for the specific system-sensor matrix, M, that corresponds to this specific temporary configuration of $N_{test}-1$ sensors;

c) replacing the sensor that was removed in step b);

d) repeating steps b) and c) a total of $N_{test}$ times;

e) identifying the specific configuration of sensors from step b) for which the condition number stored in step b) increased the least when its sensor was temporarily removed;

f) permanently removing the sensor identified in step e);

g) decrement $N_{test}$ by 1; and h) repeat steps b) through g) until the lowest condition number of the sensor placement distributions considered is less than or equal to a near-optimality criterion or until $N_{test}$ is equal to the number of sensors that are available.

17. The method of claim 16, wherein the near-optimality condition number criterion is approximately less than or equal to $10^9$ for computations in double precision.

18. The method of claim 16, wherein the near-optimality condition number criterion is such that machine round-off error is unimportant.

19. The method of claim 12, further comprising:

placing the available contaminant sensors in the determined near-optimal sensor placement distribution.

20. A system for inferring airborne contaminant concentrations in interconnected rooms without sensors from data collected by sensors located in other interconnected rooms of a building, the system comprising:

means for receiving airflow interconnectivity data for the building;

means for receiving measured contaminant concentration data from contaminant sensors in the building; and means for inferring contaminant concentration data for rooms without sensors from the flow interconnectivity data and the measured contaminant concentration data.

21. The system of claim 20 wherein the inferring means operates substantially in real time when the receiving contaminant concentration data means operates substantially in real time.

22. The system of claim 20 wherein the inferring means comprises means for solving a least squares problem.

23. The system of claim 22 wherein the means for solving a least squares problem comprises means for minimizing the sum of the squares of the difference between measured and predicted contaminant sensor concentrations and with respect to an unknown contaminant release time.

24. The system of claim 23 wherein the minimizing means is constrained to provide solutions providing non-negative initial contaminant concentrations in all rooms.

25. The system of claim 20 additionally comprising means for inferring one or more contaminant initial release points from the received and the inferred concentration data.

26. The system of claim 20 additionally comprising means for providing the received and the inferred concentration data to a system capable of determining and communicating preferred escape routes to personnel in the building.

27. A system for determining a near-optimal distribution of contaminant sensors in rooms of a building, wherein the number of contaminant sensors is less than the number of rooms in the building, wherein the system comprises:

means for determining a sensor placement distribution having a system-sensor matrix, M, that is non-singular; and means for determining the sensor placement distribution comprising determining a sensor placement distribution having the lowest condition number of all sensor placement distributions considered.

28. The method of claim 27, wherein the near-optimality condition number criterion is approximately less than or equal to $10^9$ for computations in double precision.

29. The system of claim 27, wherein the lowest condition number of the sensor placement distributions considered is small enough such that machine round-off error is unimportant.

\* \* \* \* \*